US012226672B2

(12) United States Patent
Scanlin et al.

(10) Patent No.: US 12,226,672 B2
(45) Date of Patent: Feb. 18, 2025

(54) SYSTEM AND METHOD FOR USING METABOLIC DATA TO OPTIMIZE ATHLETIC PERFORMANCE

(71) Applicant: VISION QUEST VIRTUAL, LLC, Highland Park, IL (US)

(72) Inventors: Joseph Scanlin, Milwaukee, WI (US); Robert A. Ventura, Highland Park, IL (US)

(73) Assignee: Vision Quest Virtual, LLC, Highland Park, IL (US)

( * ) Notice: Subject to any disclaimer, the term of this patent is extended or adjusted under 35 U.S.C. 154(b) by 427 days.

(21) Appl. No.: 17/837,893

(22) Filed: Jun. 10, 2022

(65) Prior Publication Data

US 2022/0395728 A1 Dec. 15, 2022

Related U.S. Application Data

(60) Provisional application No. 63/203,613, filed on Jul. 27, 2021, provisional application No. 63/209,740, filed on Jun. 11, 2021.

(51) Int. Cl.
| A63B 24/00 | (2006.01) |
| A63B 22/06 | (2006.01) |
| A63B 71/06 | (2006.01) |
| G06N 20/00 | (2019.01) |

(52) U.S. Cl.
CPC ...... *A63B 24/0006* (2013.01); *A63B 22/0605* (2013.01); *A63B 24/0062* (2013.01); *A63B 24/0075* (2013.01); *A63B 24/0087* (2013.01); *A63B 71/0622* (2013.01); *G06N 20/00* (2019.01); *A63B 2024/0009* (2013.01); *A63B 2024/0065* (2013.01);

(Continued)

(58) Field of Classification Search
CPC . A63B 24/00; A63B 24/0006; A63B 24/0003; A63B 24/0087; A63B 2024/0009; A63B 2024/0012; A63B 2024/0093; A63B 2024/0068; A63B 2024/0062; A63B 2024/0075; A63B 22/0605; A63B 22/06; A63B 71/06; A63B 71/0622; G06N 20/00
USPC .................................... 73/488–491, 379.01
See application file for complete search history.

(56) References Cited

U.S. PATENT DOCUMENTS

| 11,331,537 | B1 * | 5/2022 | Ketchell, III | ...... A63B 24/0087 |
| 11,904,207 | B2 * | 2/2024 | Bissonnette | ........... G06N 20/20 |

* cited by examiner

*Primary Examiner* — Hai L Nguyen
(74) *Attorney, Agent, or Firm* — Dickinson Wright PLLC; Jonathan H. Harder; Stephen A. Mason

(57) ABSTRACT

A method for optimizing at least one exercise is provided. The method includes receiving user data. The user data includes biometric attribute data associated with a user of an exercise device. The method includes generating at least one interval, the at least one interval including at least duration data and target power data each associated with the exercise. The method includes during the at least one interval, receiving measurement data associated with at least one of the user and the exercise device. The method includes calculating, based on the measurement data and the user data, energy data associated with an expended energy of the user during the at least one interval, the energy data including quantity data and source information each associated with at least one energy source. The method includes generating, via an artificial intelligence engine, a machine learning model trained to identify the at least one energy source.

20 Claims, 11 Drawing Sheets

(52) U.S. Cl.
CPC ............... *A63B 2024/0068* (2013.01); *A63B 2024/0093* (2013.01); *A63B 2220/13* (2013.01); *A63B 2230/75* (2013.01)

SYSTEM AND METHOD FOR USING METABOLIC DATA TO OPTIMIZE ATHLETIC PERFORMANCE

CROSS-REFERENCES TO RELATED APPLICATIONS

This application claims priority to and the benefit of U.S. Provisional Patent Application Ser. No. 63/209,740, filed on Jun. 11, 2021, titled "System and Method For Using Metabolic Data to Optimize Athletic Performance", and U.S. Provisional Patent Application Ser. No. 63/203,613 filed Jul. 27, 2021, titled "System and Method for Using Drag Force Data to Optimize Athletic Performance", the entire disclosures of which are hereby incorporated by reference for all purposes.

This application is related to of U.S. patent application Ser. No. 17/398,553 filed Aug. 10, 2021, titled "System and Method For Using Drag Force Data To Optimize Athletic Performance", which has issued as U.S. patent Ser. No. 11/331,537 on May 17, 2022, which claims priority to and the benefit of U.S. Provisional Patent Application Ser. No. 63/203,613 filed Jul. 27, 2021, and U.S. Provisional Patent Application Ser. No. 63/209,740 filed Jun. 11, 2021, the entire disclosures of which are hereby incorporated by reference for all purposes.

This application is related to PCT/US2022/025788, filed on Apr. 21, 2022, titled "System and Method For Using Drag Force Data To Optimize Athletic Performance", which claims priority to and the benefit of U.S. patent application Ser. No. 17/398,553 filed Aug. 10, 2021, which has issued as U.S. patent Ser. No. 11/331,537 on May 17, 2022, which claims priority to and the benefit of U.S. Provisional Patent Application Ser. No. 63/203,613 filed Jul. 27, 2021, and U.S. Provisional Patent Application Ser. No. 63/209,740 filed Jun. 11, 2021, the entire disclosures of which are hereby incorporated by reference for all purposes.

This application is related to U.S. patent application Ser. No. 17/745,650, filed May 16, 2022, titled "System and Method For Using Drag Force Data To Optimize Athletic Performance", which is a is a continuation of U.S. patent application Ser. No. 17/398,553 filed Aug. 10, 2021, which has issued as U.S. patent Ser. No. 11/331,537 on May 17, 2022, which claims priority to and the benefit of U.S. Provisional Patent Application Ser. No. 63/203,613 filed Jul. 27, 2021, and U.S. Provisional Patent Application Ser. No. 63/209,740 filed Jun. 11, 2021, the entire disclosures of which are hereby incorporated by reference for all purposes.

TECHNICAL FIELD

This disclosure relates generally to optimization of exercise regimens. More specifically, this disclosure relates to a system and method for using metabolic energy-system data to optimize athletic performance.

BACKGROUND

Interactive exercise regimens involve athletes performing an exercise live with one another either together in a real classroom setting or remotely in a virtual classroom setting. Each exercise is performed on an exercise device, such as a stationary bicycle, and a user interface is positioned in front of the athletes, either separate from or disposed on the exercise apparatus itself. In the virtual setting, a camera may be disposed in front of each athlete and be in communication with or a part of the user interface for transmitting and analyzing video of the athlete. To engage the user with a more competitive environment, the video is streamed, along with metric data associated with the athletes to the user interface associated with each athlete.

The metric data customarily includes speed or a distance data calculated, ultimately, from a force or pressure applied to the pedals of the stationary bike, and often referred to as "power" measured in kilojoules. Typically, the athletes are ranked according to their respective speeds or distances "traveled." By presenting the ranking of athletes on each user interface, the athletes are able to compete in order to achieve better performance and training than provided otherwise. However, various problems are created from this standard of operation, including the fact that speed, or any direct power measurement, is not the optimal metric on which to base an athlete's training. Although other metrics derived from a force on the exercise device are attainable, available exercise regimens and interfaces do not implement these other metrics in a way that encourages a competitive environment or maximizes performance while the athlete performs the exercise.

SUMMARY

Representative embodiments set forth herein disclose various techniques for enabling a system and method for using metabolic energy-system data to optimize athletic performance.

In one aspect, a method is disclosed for optimizing at least one exercise performed by a user using an exercise device is provided. The method may include receiving user data, wherein the user data includes biometric attribute data associated with the user of the exercise device. The method may also include generating at least one interval, the at least one interval including at least duration data and power data each associated with the exercise. The method may also include during the at least one interval, receiving measurement data associated with at least one of the user and the exercise device. The method may also include calculating, based on the measurement data and the user data, energy data associated with an expended energy of the user during the at least one interval, the energy data including quantity data and source information each associated with at least one energy source, and extrapolating from such measurements the energy-system utilization under various conditions, including at least one level of power and one unit of duration. The method may also include generating, via an artificial intelligence engine, a machine learning model trained to identify the at least one energy source and at least one instance of its utilization at at least one level of power output and one unit of duration.

In another aspect, a system may include a memory device storing instructions and a processing device communicatively coupled to the memory device. The processing device may execute the instructions to perform one or more operations of any method disclosed herein.

In another aspect, a tangible, non-transitory computer-readable medium may store instructions, and a processing device may execute the instructions to perform one or more operations of any method disclosed herein.

Other technical features may be readily apparent to one skilled in the art from the following figures, descriptions, and claims.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

NOTATION AND NOMENCLATURE

Figure 1:
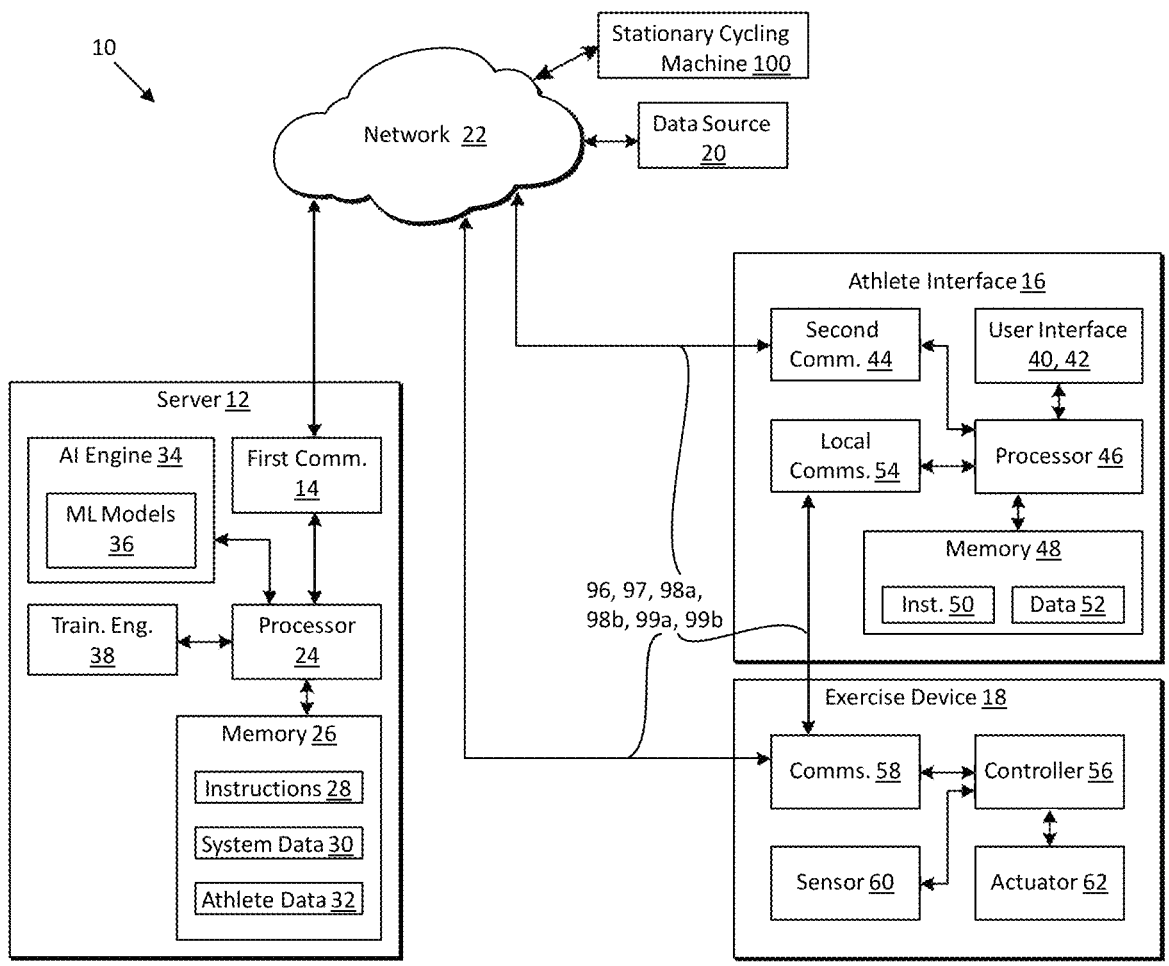
FIG. 1 generally illustrates a block diagram of an embodiment of a computer-implemented system for managing an exercise regimen according to the principles of the present disclosure.

Various terms are used to refer to particular system components. Different entities may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer or section from another region, layer or section. Terms such as "first," "second," and other numerical terms, when used herein, do not imply a sequence or order unless clearly indicated by the context. Thus, a first element, component, region, layer or section discussed below could be termed a second element, component, region, layer or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), solid state drives (SSDs), flash memory, or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

"Lactate Threshold" refers to an intensity of exercise at which lactate begins to accumulate in the blood at a higher rate than it can be removed.

"Metabolic," "energy," and "energy system" may refer to the usage by the human body of different sources of fuel for the expenditure of energy in the form of movement and force, including lipids ("fat") and glucose ("carbohydrate" or "carbs") depending on the physiology and training of the user and his or her "metabolic profile" which provides for a rational estimate of the energy system that particular individual uses to produce force at various outputs and for various durations.]

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Conventional exercise regimens involving athletes performing an exercise on an exercise device present several technical problems. One issue may involve gauging an athlete's performance based on sub-optimal metric data directly tied to a power output of the athlete, as opposed to gauging the athlete's performance on more individualized metric data tied to the metabolic profile of the athlete (such as percentage of lactate threshold). For example, one type of athlete achieving a certain speed or distance may produce entirely different and less-than-optimal results in terms of energy-system utilization and endurance than another type of athlete achieving that same speed or distance. Similarly, the posture of one athlete may be more or less aerodynamic than the posture of another athlete, and this posture is not corrected or monitored appropriately at each user interface. In addition, ranking the athletes based on force (or speed or distance mechanically derived therefrom) is not the most effective way of encouraging the most optimal competitive environment, because ranking the athletes in this way does not take into account more accurate metrics for determining individual physiological progress in the exercise regimen, such as lactate accumulation and energy-system utilization.

Another problem with conventional live workout environments relates to the presentation of live data that includes energy output and energy source data. Because metrics such as an energy source ratio (e.g. carbs to fat calories) are not presented to an interface associated with the exercise device while the athlete uses the exercise device, competitive environments based on these metrics are not available. As such, athletes have been ranked based on metrics that more directly relate to the force applied to the exercise device, such as speed and distance. Although user interfaces associated with the exercise device are capable of presenting a number of calories burned, the number is almost assuredly wrong, and typically a crude approximation based on generic estimates and limited data with respect to the user. Furthermore, the energy source of the calories (e.g., calories burned from fats vs. calories burned from carbohydrates) and the effect thereof on the athlete's individual metabolic profile is not presented to the athlete in a meaningful way while the user performs the exercise.

However, according to some embodiments of the present disclosure, energy data that includes the source and quantity of energy may be presented during the exercise regimen and may be displayed on the user data, metabolic profile, and interface associated with each athlete. Furthermore, according to some embodiments according to the present disclosure, power intervals based on this data may be generated and recommended to the athlete via the user device or via another person, such as a coach or trainer of the exercise regimen. The intervals may also or alternatively be applied in order to obtain one or more lactate threshold estimates based on the performance of the athlete during the intervals, and based on existing cohort models associated with other athletes having a common characteristic with the athlete. The optimized exercise regimen may result in the athlete being able to hold power consistently and steadily for longer periods of time. For example, the athlete's position on the exercise apparatus, the consistency of the athlete's cadence, and the rate to which the athletes accelerates to a given speed (e.g., RPM) may each be improved under an optimized exercise regimen. One goal of the disclosure, according to some embodiments, is to generate and present intervals that allow the user to hold power steady and to adjust cadence or gearing more efficiently. In this manner, the athlete may not be required to ramp up RPM, and may prevent the athlete from getting stuck with a previously proposed RPM. According to some embodiments, pedal stroke, pace, and, ultimately, a power curve associated with the exercise regimen may be smoothed out via gamifications in the software, such as ranking, rewards, etc.

The disclosed subject matter provides a technical solution to a technical problem in numerous ways. For example, the disclosed embodiments provide an enhanced user interface that provides information to a user in an enhanced way that improves the user's experience of using a computing device, thereby providing a technical improvement. The information may include additional metrics, such as blood lactate, that enables the user to perform and compete in an optimal manner using the exercise machine. Further, the enhanced exercise regimens that are generated may enable controlling the exercise device in a manner that reduces the wear-and-tear of the device and may extend the useful life of the exercise device. Additionally, certain modes of operation of the exercise device may include remote virtual sessions, where a video feed of a coach is presented on the user interface of the exercise device. This technical capability may provide a technical solution to the problem of when the user and the coach are physically unable to be present in a same location (e.g., due to a pandemic or living in different states, etc.).

In some embodiments, the systems and methods described herein may be configured for optimizing at least one exercise for a user using an exercise device. In some embodiments, the systems and methods described herein may be configured to receive user data, wherein the user data includes biometric attribute data associated with a user of an exercise device. In some embodiments, the systems and methods described herein may be configured to generate at least one interval, the at least one interval including at least duration data and target power data each associated with at least one exercise performed by the user using an exercise device. In some embodiments, the systems and methods described herein may be configured to, during the at least one interval, receive measurement data associated with at least one of the user and the exercise device. In some embodiments, the systems and methods described herein may be configured to calculate, based on the measurement data and the user data, energy data associated with an expended energy of the user during the at least one interval, the energy data including quantity data and source information each associated with at least one energy source. In some embodiments, the systems and methods described herein may be configured to generate, via an artificial intelligence engine, a machine learning model trained to identify the at least one energy source.

In some embodiments, the systems and methods described herein may be configured to present, on a user interface associated with the exercise, the quantity data and source information associated with at least one identified energy source.

In some embodiments, the at least one identified energy source includes at least one of a carbohydrate and a lipid. By way of example, in some embodiments, an identification of "carbohydrates" being the at least one energy source allows the system to identify that the user is utilizing lactic capacity, and thereby improving the user's "gas tank."

In some embodiments, the systems and methods described herein may be configured to calculate an energy source ratio, the energy source ratio being defined by a ratio of the quantity data associated with one of the at least one identified energy source to the quantity data associated with another one of the at least one identified energy source. In some embodiments, the systems and methods described herein may be configured to present the energy source ratio on the user interface while the user performs the exercise.

In some embodiments, the systems and methods described herein may be configured to generate, via an artificial intelligence engine and based on the measurement data and the user data, a machine learning model trained to identify lactate accumulation data associated with the lactate accumulation of the user while the user uses the exercise device. In some embodiments, the systems and methods described herein may be configured to present the lactate accumulation data on the user interface while the user performs the exercise.

In some embodiments, the systems and methods described herein may be configured to generate, via an artificial intelligence engine and based on the measurement data and the user data, a machine learning model trained to identify lactate threshold data associated with a lactate threshold of the user. In some embodiments, the systems and methods described herein may be configured to present, on the user interface, the lactate threshold data while the user performs the exercise.

In some embodiments, the at least one interval includes a first interval and a second interval, and wherein either the duration data associated with the first interval is different than the duration data associated with the second interval or the target power data associated with the first interval is different than the target power data associated with the second interval.

In some embodiments, the systems and methods described herein may be configured to determine a first level of compliance associated with an identifier of a first user performing the exercise. In some embodiments, the systems and methods described herein may be configured to determine a second level of compliance associated with an identifier of a second user performing the exercise. In some embodiments, the systems and methods described herein may be configured to present the identifier of each of the first user and the second user on a user interface associated with the exercise. In some embodiments, the systems and methods described herein may be configured to position, based on a difference between the first level of compliance and the second level of compliance, the identifier of the first user in relation to the identifier of the second user on the user interface while the user performs the exercise.

In some embodiments, the systems and methods described herein may be configured to generate a target position of the user, the target position corresponding to an aerodynamic position of the user associated with the at least one interval. In some embodiments, the systems and methods described herein may be configured to monitor an actual position of the user during the at least one interval. In some embodiments, the systems and methods described herein may be configured to calculate differential data based on a difference between the actual position of the user and the target position of the user. In some embodiments, the systems and methods described herein may be configured to transmit the differential data to the user while the user performs the exercise.

In some embodiments, the systems and methods described herein may be configured to presenting, on a user interface, the differential data concurrently with an instruction guiding the actual position of the user to the target position of the user.

Generating an enhanced cardiovascular tailored workout may include applying the theory of stress and response to an exercise regimen in an optimal way. In some embodiments, a software application may be implemented to deliver the best training for progressing an athlete's skill development and for progressing the athlete's physiological functions, such as muscle mass, response time, etc. Accordingly, the software, according to some embodiments of the present disclosure, may be implemented in computer instructions that, when executed by a processing device, process power data as well as recovery data associated with the exercise regimen. For example, incorporating data provided from a set of devices, such as a mobile device configured to track resting heart rate, heart rate, sleep pattern and duration, temperature, and blood glucose levels may allow the software to determine an overall energy availability of the athlete. By incorporating actual energy availability, the next interval or other portion of the exercise regimen may be modified to fit that particular athlete's actual energy availability. Additionally or alternatively, the software may present a questionnaire to the athlete to receive the recovery data and the power data prior to or during the exercise regimen.

In some embodiments, experimental tests may be applied during intervals in order to determine conditions in which the athlete has improved performance. For example, modifying the ambient air temperature using cooling devices, such as fans, and heating devices and applying the interval at various temperatures may allow the artificial intelligence engine to identify optimal conditions.

The software may also teach athletes how to exercise more effectively and efficiently, for example, in a more aerodynamic position. In the aerodynamic position, the athlete may have an increased speed at the same power output. By providing the intervals, athletes may improve at stressing themselves in a more aerodynamic position to maximize power output. A front-facing camera may be implemented in order to gather positional data of the athlete during an interval. The camera may be connected to or integrated with a computer or tablet, such as an iPad®, and the software application may be configured to activate and access the video data recorded by the camera. Using computer vision software and machine learning models with the video data from the camera, a user's deviation or compliance with an aerodynamic position can be determined with only a frontal view of the user. It should be appreciated that several views may be captured by the camera and interpreted by the computer vision software to determine compliance with an aerodynamic position. Via a sensor placed on the exercise device, a status of a gear ratio of the exercise device may be monitored. Based on the level of positional compliance and the gear ratio status, the exercise device may be controlled to change the gear ratio via an actuator, or a coach of the exercise regimen or user interface may instruct the athlete to change the gear ratio.

One important facet of generating an improved training plan is identifying strengths and weaknesses associated with the athlete. More specifically, identifying the state of the athlete's muscular system and cardiovascular system, as well as identifying the athlete's aerobic and anaerobic capacity, allows the coach or the software to target the systems and capacities that need improvement. According to at least some embodiments of the present disclosure, this can be done by applying various power intervals, recording power output data (e.g., speed and acceleration data associated with the athlete performing the exercise) and/or at least one biometric attribute associated with the athlete. Once the physiological strengths and weaknesses are identified, the artificial intelligence engine may implement machine learning models to suggest different exercise regimens and/or additional power intervals. The additional power intervals may thus be curtailed to improve that particular athlete's weakness.

By way of example, an athlete may perform a power interval requiring a 30% power output, or a 30 percent energy output, for a duration of 15 minutes. In real time, the athlete's actual power output (e.g., speed) is tracked and, upon completing the power interval, is analyzed by the software. The analysis may reveal that, for the first 5 minutes of the workout, the athlete was working "too hard" (e.g., utilizing aerobic capacity or expending energy from the muscular system), while the latter 10 minutes were associated with cardiovascular capacity at lower intensity. This deviation from the ideal interval allows the software to detect that the athlete's weakness is related to pacing to maximize cardio output. The machine learning models are trained using at least cohort data to generate a particularized exercise regimen that targets improvement of cardio output. As a result, a power interval requiring 25% power output over 20 minutes, for example, may be recommended. Based on the timeline data of the original power interval, the user interface may be configured to present a message at specific times of the new interval to remind the user to ramp up or ramp down the athlete's speed. It should also be appreciated that the power intervals in this example may require a lactate threshold or a metabolic profile as opposed to a VO2 Maximum power, a functional power threshold (FTP), or a raw speed. This is a non-limiting example, and other examples of how the software identifies the strengths and weaknesses may be derived from or local deductions of what has been described.

In addition to the above example directed to particularized exercise regimens, group-wide exercise regimens (i.e., exercises for simultaneous performance by multiple athletes) may be generated. The group-wide exercise regimens may have a common target for each athlete, where the common target is related to a metabolic profile associated with each athlete, or a lactate threshold associated with each athlete. Each athlete participating in the class may be expected to produce the same exact stress because the stress may be based off of a metric consistent across each athlete's energy system (e.g., intensity, lactate threshold, or amount of blood lactate produced).

Whether the exercise is performed in an individual or group environment, in some embodiments according to the present disclosure, the source and associated quantity of the athlete's energy expended during the exercise may be identified. The source may be identified based on a history of power intervals previously applied and/or blood glucose levels retrieved immediately following one or more power intervals, combined with the data received during the real-time exercise. Additionally or alternatively, the energy data is correlated in such a manner that generally higher intensity workouts correspond to burning more carbohydrates or sugar, and lower intensity workouts correspond to burning more fat. By measuring how hard the athlete can exercise for a given time period, the source and quantity of calories may be determined. The amount of energy (e.g., number of calories) burned from each source, such as fats or lipids, carbohydrates (e.g., sugars), and proteins is ascertained in a similar manner (e.g., accurate estimations based on prior data and/or machine learning models and/or known correlations). As such, various ratios may be calculated, such as fat to carb calories currently or cumulatively burned during the exercise. The energy data, including the energy source and quantity data, can be presented on the user interface associated with each athlete. The particular presentation of this data is discussed below with reference to FIGS. 4-5, but other manners of presenting this data in real-time may be provided.

Exercise regimens according to the present disclosure may be based on lactate threshold. Lactate is generated from the anaerobic system and is used ultimately by the aerobic system. By tracking a level of lactate in an athlete's body after a series of intervals with various power requirements (i.e., work over time), a lactate threshold associated with the athlete may be identified. Traditionally, this may be done by physically testing the athlete's blood to identify the amount of lactate in the athlete's blood; however, accurate estimations according to the present disclosure may be identified via the machine learning models. Iterating the physical process across a multitude of athletes having different characteristics, including body weight, height, sex, body fat ratio, sleep patterns, resting heart rate, heart rate variability, blood glucose level, body temperature, ambient air temperature, etc., provides a large quantity of data capable of storage in a data base, such as data source 20. Based on that data, the machine learning model may generate a set of exercise regimens that correlate to an athlete having a minimal amount of user characteristics. In other words, the machine learning models may be trained to recommend an exercise regimen to an athlete based on only as few as one or two characteristics of the user, and as a result of the iterative process. These characteristics may be biological metrics, such as blood glucose or body fat percentage, but alternatively or additionally may be characteristics identified after one or more power intervals have been performed by the athlete on the exercise device and monitored. Presenting the energy source data and the metabolic profile to the user in real-time (e.g., during the exercise) and allowing the artificial intelligence engine to analyze real-time feedback may provide an immersive, competitive, and overall optimal workout to the user.

In some embodiments, an estimate of the energy expenditure across the full range of power outputs and durations (e.g., metabolic power curves on a graph) may be obtained and determined. In some embodiments, measuring the critical interval(s) may enable generating a curve on a graph and using the curve to generate real-time fat/carb/lactate measurements and assessing compliance and prescribing training for improvement. In some embodiments, artificial intelligence engine may identify the utilization of at least one energy source at at least one intensity and at least one duration based on the user's individual biometric attribute data.

In some embodiments, one or more recommendations may be generated for exercises or training based on the results determined by the techniques disclosed herein. The one or more recommendations may be generated in view of a desired improvement or goal of the user (e.g., increased endurance, power output, speed, or any suitable energy system utilization, etc.). In some embodiments, the user's performance may be tracked via one or more sensors against the desired improvement or goal in real-time and adjustments may be made to the recommendations based on progress toward the desired improvement or goal. The artificial intelligence engine may train a machine learning model to generate the one or more recommendations and/or the perform the adjustments.

FIG. 1 generally illustrates a block diagram of a computer-implemented system 10, hereinafter called "the system" for managing an exercise regimen. Managing the exercise regimen may include using an artificial intelligence engine to recommend exercise regimens and/or provide excluded exercise regimens that should not be recommended to an athlete. In some embodiments, the artificial intelligence engine may be configured to control an exercise device 18.

The system 10 also includes a server 12 configured to store (e.g. write to an associated memory) and to provide data related to managing the exercise regimen. The server 12 may include one or more computers and may take the form of a distributed and/or virtualized computer or computers. The server 12 also includes a first communication interface 14 configured to communicate with at least one athlete interface 16, at least one exercise device 18 associated with the at least one athlete interface 16, and a data source 20 via at least one network 22. In some embodiments, the at least one network 22 may include a local area network (LAN), such as an Ethernet network, and communications between the at least one athlete interface 16 and the server 12. The communications may be secured via encryption, such as, for example, by using a virtual private network (VPN). In some embodiments, the at least one network 22 may include wired and/or wireless network connections such as Wi-Fi, Bluetooth, ZigBee, Near-Field Communications (NFC), cellular data network, etc. Additionally or alternatively, the at least one network 22 may include a set of networks in communication with one another.

The server 12 includes a first processor 24 and a first machine-readable storage memory 26, which may be called a "memory" for short, holding first instructions 28 for performing the various actions of the server 12 for execution by the first processor 24. The server 12 is configured to store data regarding the exercise regimen. For example, the memory 26 includes a system data store 30 configured to hold system data, such as data pertaining to exercise regimens for training one or more athletes. The server 12 is also configured to store data regarding performance by an athlete in following an exercise regimen. For example, the memory 26 includes an athlete data store 32 configured to hold athlete data, such as data pertaining to the one or more athletes, including data representing each athlete's performance within the exercise regimen.

Additionally or alternatively, the characteristics (e.g., personal, performance, measurement, etc.) of the athletes, the exercise regimens followed by the athletes, the level of compliance with the exercise regimens, and the results of the exercise regimens may use correlations and other statistical or probabilistic measures to enable the partitioning of or to partition the exercise regimens into different athlete cohort-equivalent databases in the athlete data store 30. For example, the data for a first cohort of first athletes having a first metabolic rate, a first exercise regimen followed by the first athlete, and a first result of the exercise regimen may be stored in a first athlete database. The data for a second cohort of second athletes having these similar characteristics may be stored in a second athlete database. Any single characteristic or any combination of characteristics may be used to separate the cohorts of athletes. In some embodiments, the different cohorts of athletes may be stored in different partitions or volumes of the same database. There is no specific limit to the number of different cohorts of athletes allowed, other than as limited by mathematical combinatoric and/or partition theory.

This characteristic data, training plan data, and results data may be obtained from numerous exercise devices and/or computing devices and/or digital storage media over time and stored in the data store 30. The characteristic data, training plan data, and results data may be correlated in the athlete-cohort databases in the data store 30. The characteristics of the people may include personal information, performance information, and/or measurement information.

In addition to the historical information about other people stored in the athlete cohort-equivalent databases, real-time or near-real-time information based on the current athlete's characteristics about a current athlete being treated may be stored in an appropriate athlete cohort-equivalent database. The characteristics of the athlete may be determined to match or be similar to the characteristics of another person in a particular cohort (e.g., cohort A) and the athlete may be assigned to that cohort.

In some embodiments, the server 12 may execute an artificial intelligence (AI) engine 34 that uses one or more machine learning models 36 to perform at least one of the embodiments disclosed herein. The server 12 may include a training engine 38 capable of generating the one or more machine learning models 36. The machine learning models 36 may be trained to assign people to certain cohorts based on their characteristics, select exercise regimens using real-time and historical data correlations involving athlete cohort-equivalents, and control the exercise device 18, among other things. The one or more machine learning models 36 may be generated by the training engine 38 and may be implemented in computer instructions executable by one or more processing devices of the training engine 38 and/or the servers 12. To generate the one or more machine learning models 36, the training engine 38 may train the one or more machine learning models 36. The one or more machine learning models 36 may be used by the artificial intelligence engine 34.

The training engine 38 may be a rackmount server, a router computer, a personal computer, a portable digital assistant, a smartphone, a laptop computer, a tablet computer, a netbook, a desktop computer, an Internet of Things (IoT) device, any other suitable computing device, or a combination thereof. The training engine 38 may be cloud-based or a real-time software platform, and it may include privacy software or protocols, and/or security software or protocols.

To train the one or more machine learning models 36, the training engine 38 may use a training data set of a corpus of the characteristics of the athletes that used the exercise device 18 to perform exercise regimens, the details of the exercise regimens performed by the athletes using the exercise device 18, and the results of the exercise regimens performed by the athletes. The one or more machine learning models 36 may be trained to match patterns of characteristics of an athlete with characteristics of other athletes assigned to a particular cohort. The one or more machine learning models 36 may be trained to receive the characteristics of an athlete as input, map the characteristics to characteristics of athletes assigned to a cohort, and select an exercise regimen from that cohort. Different machine learning models 36 may be trained to recommend different exercise regimens for different desired results. For example, one machine learning model may be trained to recommend exercise regimens for maximizing cardiovascular output, while another machine learning model may be trained to recommend exercise regimens for maximizing aerobic or anaerobic output.

The one or more machine learning models 36 may comprise, e.g., a single level of linear or non-linear operations (e.g., a support vector machine [SVM]) or the machine learning models 36 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The athlete interface 16 is configured to communicate information to an athlete and to receive feedback from the athlete. Specifically, the athlete interface 16 includes an input device 40 and an output device 42, which may be collectively called an athlete user interface 40, 42. The input device 40 may include one or more devices, such as a keyboard, a mouse, a touch screen input, a gesture sensor, a camera, and/or a microphone and processor configured for voice recognition. The output device 42 may take one or more different forms including, for example, a computer monitor or display screen on a tablet, smartphone, or a smart watch. The output device 42 may include other hardware and/or software components such as a projector, virtual reality capability, augmented reality capability, etc. The output device 42 may incorporate various different visual, audio, or other presentation technologies. The output device 42 may comprise one or more different display screens presenting various data and/or interfaces or controls for use by the athlete. The output device 42 may include graphics, which may be presented by a web-based interface and/or by a computer program or application (App.). In some embodiments, the user interface 42 may include functionality provided by or similar to existing voice-based assistants such as Siri® by Apple®, Alexa® by Amazon®, Google Assistant®, or Bixby® by Samsung®.

As generally illustrated in FIG. 1, the user interface 16 includes a second communication interface 44, which may also be called a remote communication interface, configured to communicate with the server, the at least one exercise device 18 associated with the at least one athlete interface 16, and the data source 20 via the at least one network 34.

The athlete interface 16 includes a second processor 46 and a second machine-readable storage memory 48 holding second instructions 50 for execution by the second processor 46 for performing various actions of athlete interface 16. The second machine-readable storage memory 48 also includes a local data store 52 configured to hold data, such as data pertaining to an exercise regimen and/or athlete data, such as data representing an athlete's performance within an exercise regimen.

Additionally or alternatively, the athlete interface 16 includes a local communication interface 54 configured to communicate with various devices for use by the athlete in the vicinity of the athlete interface 16. The local communication interface 54 may include wired and/or wireless communications. In some embodiments, the local communication interface 68 may include a local wireless network such as Wi-Fi, Bluetooth, ZigBee, Near-Field Communications (NFC), cellular data network, etc.

The exercise device 18 is configured to be manipulated by the athlete and/or to manipulate a body part of the athlete for performing activities according to the exercise regimen. In some embodiments, the exercise device 18 may take the form of an exercise device 18 configured to perform a training regimen associated with cycling, walking, jogging, etc. For example, in some embodiments similar to that shown in FIG. 2, the exercise device 18 is a stationary bicycle. The exercise device 18 may be any suitable exercise device 18 configured to be controlled distally via another computing device to train an athlete and/or exercise the athlete. The exercise device 18 may be an electromechanical machine including one or more weights, an electromechanical bicycle, an electromechanical spin-wheel, a treadmill, an interactive environment system or the like.

As generally illustrated in FIG. 1, the exercise device 18 includes a controller 56, which may include one or more processors, computer memory, and/or other components. The exercise device 18 also includes a fourth communication interface 58 configured to communicate with the athlete interface 16 via the local communication interface 54. The exercise device 18 also includes one or more sensors 60 and, in some embodiments, an actuator 62, such as a motor. The actuator 62 may be used, for example, for moving the athlete's body part and/or for resisting forces by the athlete.

The sensors 60 may measure one or more operating characteristics of the exercise device 18 such as, for example, a force, a position, a speed, and/or a velocity. In some embodiments, the sensors 60 may include a position sensor configured to measure at least one of a linear motion or an angular motion of a body part of the athlete. For example, a sensor 60 in the form of a position sensor may measure a distance that the athlete is able to move a part of the exercise device 18, where such distance may correspond to a range of motion that the athlete's body part is able to achieve. In some embodiments, the sensors 60 may include a force sensor configured to measure a force applied by the athlete. For example, a sensor 60 in the form of a force sensor may measure a force or weight the athlete is able to apply, using a particular body part, to the exercise device 18.

The data source 20 may include data provided by a mobile device configured to track biometric data associated with a user of the exercise device 18. For example, the mobile device may be in communication with an ambulation sensor configured to track and store a number of steps taken by the user. In some embodiments, the ambulation sensor may take the form of a wristband, wristwatch, or smart watch. In some embodiments, the ambulation sensor may be integrated within the mobile device a phone, such as a smartphone. Data may be provided from a device, such as a pulse oximeter or a glucometer, configured to analyze the composition of the athlete's blood, such as a blood glucose level. In some embodiments, the athlete data is gathered and machine learning models are generated based on utilizing this device across a set of athletes after each athlete has performed a particular power interval.

Additionally or alternatively, the at least one user interface may include a first user interface and a second user interface. The at least one exercise device 18 may include a first exercise device associated with the first user interface and a second exercise device associated with the second user interface. In this manner, data may be communicated via the network to and from a set of user interfaces with the exercise device 18 associated with each user interface. Likewise, the system may be configured to accommodate a set of athletes, for example, a first athlete and a second athlete, where the first athlete is associated with the first user interface and the first exercise apparatus, and where the second athlete is associated with the second user interface and the second exercise apparatus. The second athlete may be coach of a workout being performed on each exercise device. The coach may have access, via the coach's user interface, to specific functions unavailable to the other athletes.

Various devices of the system, such as the server 12, the user interface 16, the exercise device 18, and the data source 20 are configured to communicate device control signals 99a and device monitor signals 99b associated with the athlete using the athlete interface 16 and/or the exercise device 18. The device control signals 99a and device monitor signals 99b may comprise at least one of an audio signal 96, an audiovisual signal 97, an interface control signal 98a for controlling a function of the athlete interface 16, an interface monitor signal 98b for monitoring a status of the athlete interface 16, a device control signal 99a for changing an operating parameter of the exercise device 18, and/or an apparatus monitor signal 99b for monitoring a status of the exercise device 18. In some embodiments, each of the control signals 98a, 99a may be unidirectional, conveying commands from a second user interface associated with the coach to the athlete interface 16. In some embodiments, in response to successfully receiving a control signal 98a, 99a and/or to communicate successful and/or unsuccessful implementation of the requested control action, an acknowledgement message may be sent from the athlete interface 16 to the coaching interface. In some embodiments, each of the monitor signals 98b, 99b may be unidirectional, status-information commands from the athlete interface 16 to the coach interface. In some embodiments, an acknowledgement message may be sent from the coach interface to the athlete interface 16 in response to successfully receiving one of the monitor signals 98b, 99b.

In some embodiments, the athlete interface 16 may be configured as a pass-through for signals 96, 97, 98a, 98b, 99a, 99b between the exercise device 18 and one or more other devices, such as the server 12. For example, the athlete interface 16 may be configured to transmit a device monitor signal 99b from the local communication interface 54 to the server 12 via the at least one network 22 in response to receiving the device monitor signal 99b from the local communication interface 58 of the exercise device 18. Alternatively, the device control signals 99a and the device monitor signals 99b may be sent directly to the server 12 via the network 22.

In some embodiments, the athlete interface 16, the server 12, and/or the exercise device 18 may be configured to communicate and/or control an exercise machine 100. The stationary cycling machine 100 may include a communication interface (capable of communicating data via any suitable network protocol, WiFi, the Internet, Bluetooth, Ethernet, etc.), a processing device (capable of executing computer instructions), and/or a memory device (capable of storing computer instructions to perform any operation described herein). The stationary cycling machine 100 is described further herein.

Figure 2:
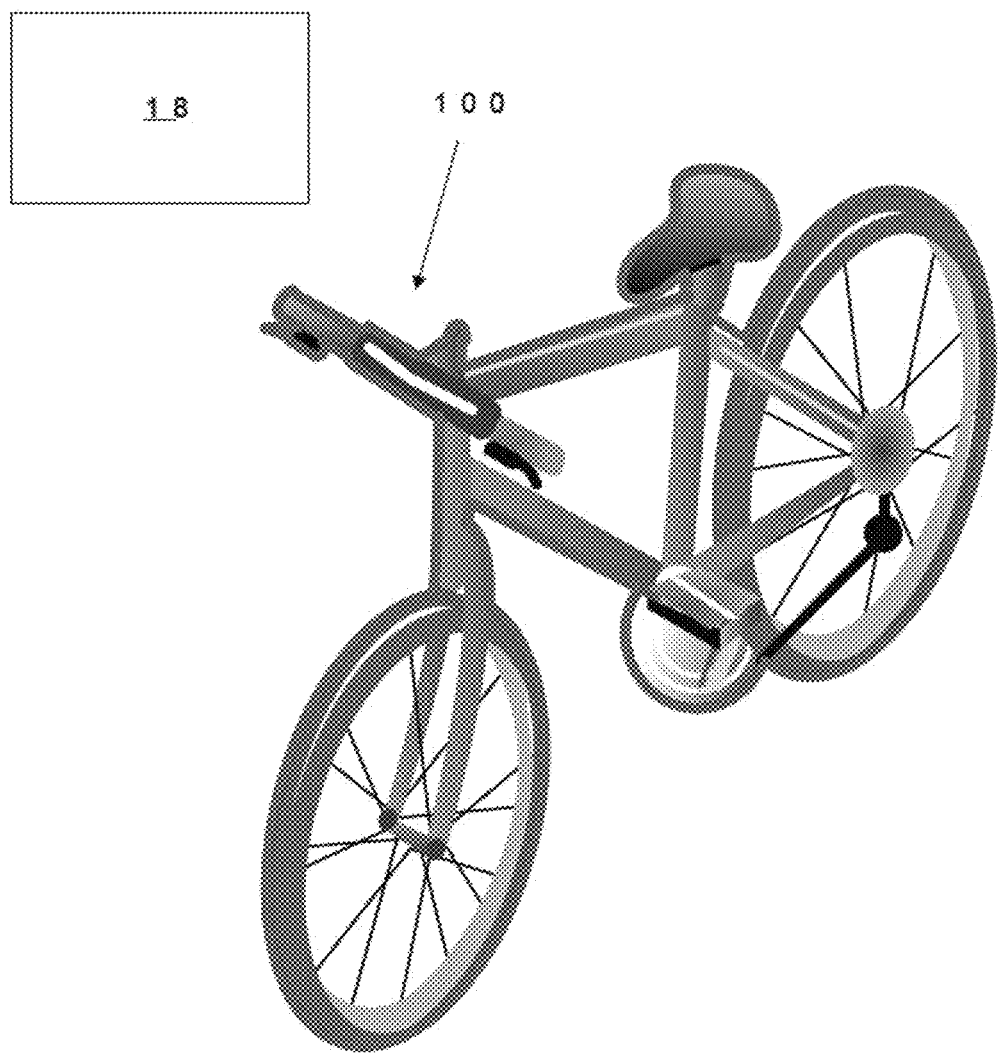
FIG. 2 generally illustrates a perspective view of an embodiment of an exercise device according to the principles of the present disclosure.
Figure 3:
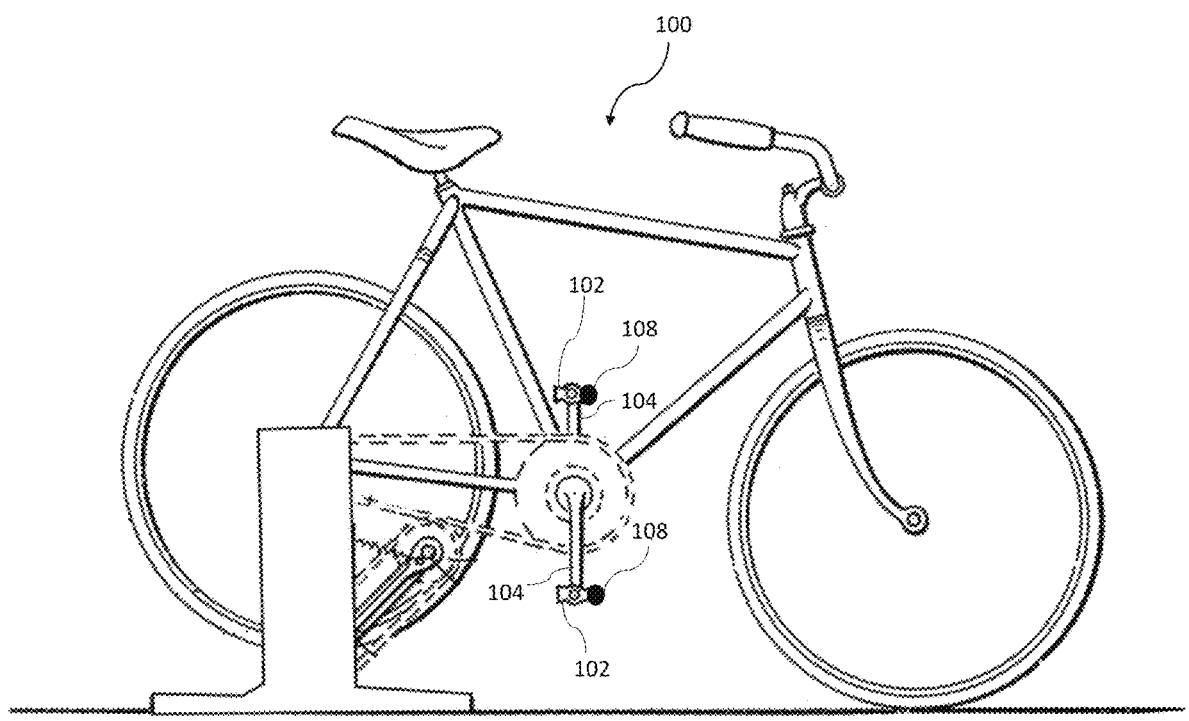
FIG. 3 generally illustrates a perspective view of an embodiment of an exercise device according to the principles of the present disclosure.

FIGS. 2-3 generally illustrate an exercise apparatus 18 in the form of a stationary cycling machine 100, which may be referred to as a stationary bike herein. The stationary cycling machine 100 includes a set of pedals 102 each attached to a pedal arm 104 for rotation about an axle 106. In some embodiments, and as generally illustrated in FIG. 2, the pedals 102 are movable on the pedal arms 104 in order to adjust a range of motion used by the athlete in pedaling. For example, the pedals being located inwardly toward the axle 106 corresponds to a smaller range of motion than when the pedals are located outwardly away from the axle 106. One or more pressure sensors 108 may be attached to or embedded within one or both of the pedals 102 for measuring an amount of force applied by the patient on a pedal 102. The pressure sensor 108 may communicate wirelessly to the exercise apparatus 18 and/or to the patient interface 16. As generally illustrated in FIG. 3, the athlete interface 16 may be disposed near the front of the exercise apparatus 18. In some embodiments, the athlete interface 16 is attached to or disposed on the exercise direction to allow the athlete to interact with the athlete interface 16.

Figure 4:
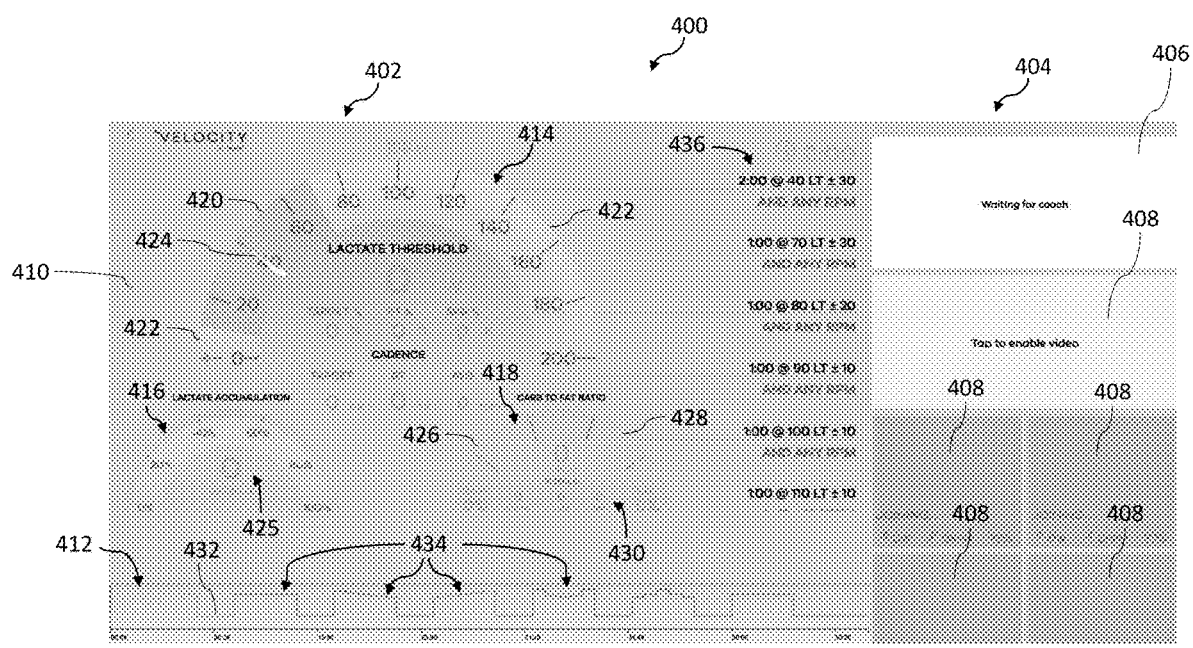
FIG. 4 generally illustrates an example embodiment of a display of a user interface according to the principles of the present disclosure.
Figure 5:
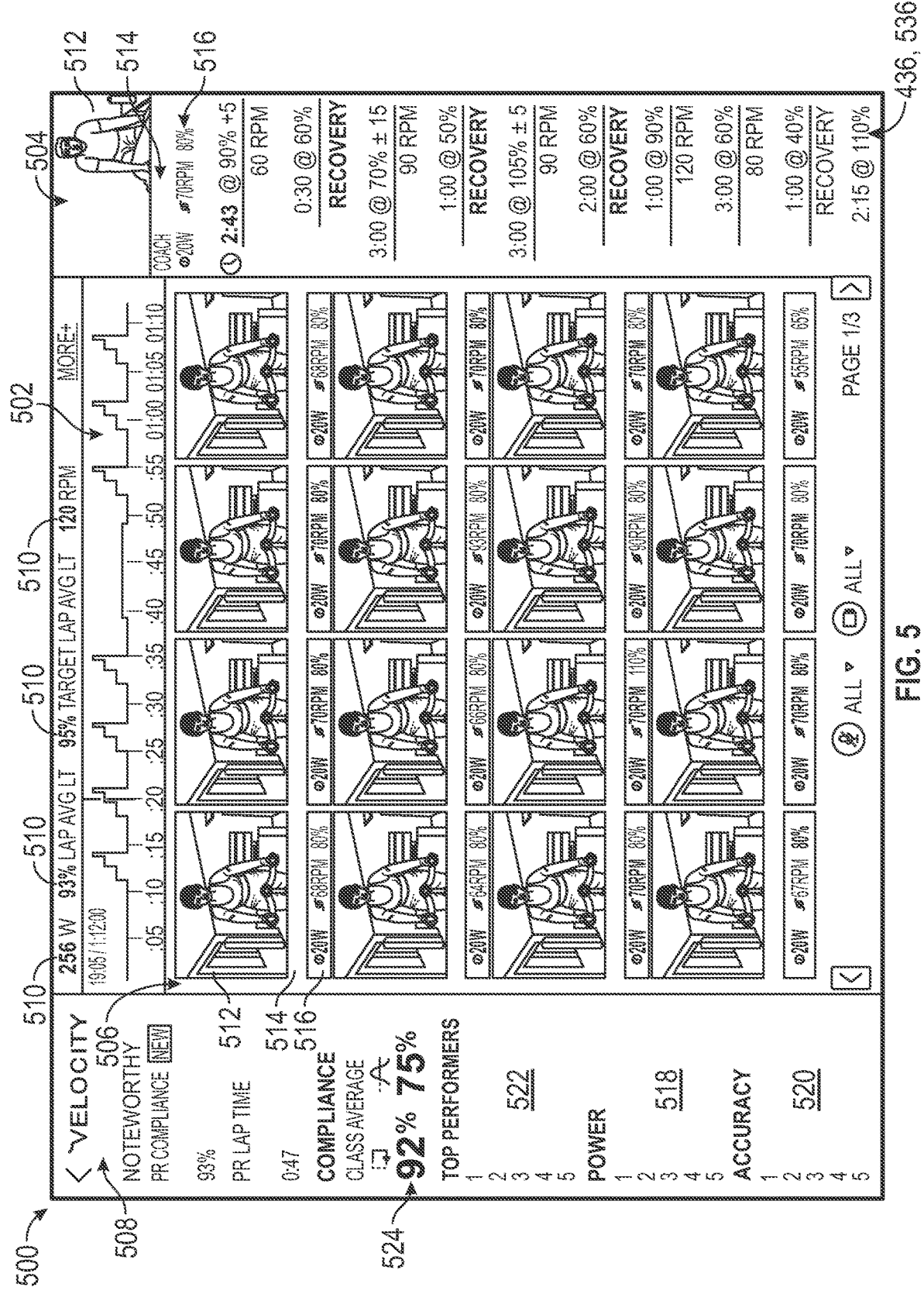
FIG. 5 generally illustrates an example embodiment of a display of a user interface according to the principles of the present disclosure.

FIGS. 4-5 are example embodiments of at least one display 400, 500 for presenting on the user interface. More specifically, FIG. 4 is an example embodiment of a first display, referred to as an athlete display 400, according to an embodiment of the present of the present disclosure, and FIG. 5 is an example embodiment of a second display, referred to as a coach display 500, according to an embodiment of the present disclosure. In operation, the user may toggle between each of the athlete display 400 and the coach display 500.

The athlete display 400 includes a first portion 402 for presenting various metrics associated with the user while the user performs the exercise associated with the exercise apparatus 18. A second portion 404 is also presented adjacent to the first portion 402 and including a set of first windows 406, 408, such as a coach window 406 and at least one athlete window 408. The coach window 406 and at least one athlete window 408 are configured to present an image, a live-stream, or a prerecorded video of the user, at least some other athletes, and the coach participating in the workout. Within each of the set of first windows 406, 408 is at least one metric associated with the athlete. In this manner, the user may view the status of the other athletes and compare the user's progress in the exercise regimen to the progress of the other athletes.

The first portion 402 of the athlete display 400 includes a gauge display 410 and a timeline display 412 disposed adjacent to the gauge display 410. The gauge display 410 includes main gauge 414, as well as first and second secondary gauges 416, 418 displayed on either side of the main gauge 414. The main gauge 414 provides for presenting lactate threshold data, generally in the unit of watts (e.g., power), corresponding to the lactate threshold of the user. Lactate threshold data, including a target lactate threshold percentage, a real-time lactate threshold percentage (e.g., relative to an ideal compliance), and an average lactate threshold is presented in the gauge area adjacent to the main gauge 414. Cadence data including a target cadence, a real-time cadence percentage (e.g., relative to an ideal compliance), and an average lactate threshold is presented in the gauge area adjacent to the main gauge 414. The lactate threshold data and the cadence data correspond to the user's performance relative to an already-identified threshold, determined via previously-gather data based on previous power intervals and/or biometric data of the user. Presenting the lactate threshold data in the form of the main gauge 414, with the gauge presenting different regions 420, 422 associated by color, allows the user to track his/her performance in view of the required interval. One region 420, for example in the range of 15 W-65 W, may be presented with a purple hue or other color provided for encouraging the user to maintain a particular lactic threshold. A needle 424 is presented on the main gauge 414 to indicate the user's real-time lactate threshold.

The first secondary gauge may be presented as a lactate accumulation gauge 416, positioned left of the main gauge 414, and the second secondary gauge may be presented as an energy source gauge 418, positioned right of the main gauge 414. The lactate accumulation gauge 416 and the energy source gauge 418 each operate in a similar manner to the main gauge 414 with respect to presenting a needle (not shown) or a color in a region of the gauges for indicating the current measurement. Lactate accumulation or lactate accumulation rate of the user may be presented on the lactate accumulation gauge 416, and a quantity or percentage of calories from carbohydrates being burned relative to calories burned from fats may be presented additionally or alternatively.

With respect to the lactate accumulation gauge 416, a percentage of lactate accumulation associated with the user while the user uses the exercise apparatus is presented as a percentage, as shown in FIG. 4. However, other similar metrics and/or units associated with lactate accumulation may be shown, such as lactate accumulation rate. Additionally or alternatively, lactate accumulation rate data 425 may be presented in the form of a number of millimoles per minute that the user's body is currently producing. The lactate accumulation rate data my by presented alongside or below the lactate accumulation gauge 416, as illustrated in the example embodiment. As discussed throughout this disclosure, the data lactate accumulation data and lactate accumulation rate data correspond to the user's performance relative to an already-identified lactate threshold or lactate accumulation rate, determined via previously-gather data based on previous power intervals and/or biometric data of the user.

With respect to the energy source gauge 418, as illustrated in the example embodiment of FIG. 4, two percentages, in some cases totaling at or about 100%, are presented in separate regions 426, 428 of the gauge. The two percentages, are associated with first energy source data (e.g., percentage of energy being burned from carbohydrates) and second energy source data (e.g., percentage of energy being burned from fats). Because the total of each will generally be 100%, the energy source gauge 418 may define a moving edge (not shown) between the regions corresponding to an energy source ratio (e.g., carb to fat ratio) to illustrate a ratio of energy (e.g., calories) currently being burned from carbohydrates relative to those being burned from fats. A current amount of energy being expended per unit of time (e.g. calories per hour) may be presented adjacent to the energy source gauge 418. In addition, totals data 430 may be presented adjacent to the energy source gauge 418 indicating, for example, how many calories have been burned from fats or carbohydrates since the workout started, as well as a total of both. As discussed throughout this disclosure, the energy source data corresponds to the user's metabolic profile, which is based on an already-identified lactate threshold or lactate accumulation rate gathered via previous power intervals and/or biometric data of the user. Having refined a metabolic profile of the athlete, the carb-to-fat ratio may be accurately estimated by factoring in the athlete's current performance.

The timeline display 412 according to the example embodiment illustrated in FIG. 4 is presented below the gauge display 402 and presents performance data 432 of the user over time. As illustrated, patterns 434 may be generated corresponding to the various intervals. Just as the user and coach may view the performance data 432, the artificial intelligence engine 34 may access this data to identify trends, including strengths and weaknesses associated with the user. The machine learning models 36 may be trained to generate ideal exercise regimens for the user based on these strengths and weaknesses, as discussed throughout the present disclosure.

An interval list display 436 is presented alongside the gauge display 402 to indicate future and/or past scheduled power intervals. Each item of the interval list display 436 may include duration data and target power data, as well as deviation range (e.g., +/−30). The target power data may be presented in the form as lactate threshold, as illustrated in the example embodiment. The interval list display 436 may also present a speed (e.g. rotations per minute) for the user to perform, or may allow the user to choose the RPM. This is largely due to the fact that the athletes are, in some embodiments, ranked according to a level of compliance with energy usage as opposed to raw power output. Further, regardless of ranking and in some embodiments, analyzing performance based on RPM is an inferior way of training the athlete relative to tracking energy output and source.

In some embodiments, a position compliance may be presented on the athlete display. The position compliance is based on the athlete's physical position on the exercise device 18 compared to an ideal position of the athlete on the device 18. The athlete's physical position may be determined based on a front-facing or other view-associated camera in communication with or otherwise connected to the athlete interface 16. Video data provided by the front-facing camera, may be compared to ideal positional data stored on the server 12, the athlete interface 16, or any other component shown or described in FIG. 1. Differential data may be generated based on the comparison, and presented to the user in the form of a compliance score. Additionally or alternatively, the athlete display 400 may include a video of the athlete along with an overlaid outline of the ideal position. The ideal position may correspond to an optimal aerodynamic position for outdoor riding.

The user interface depicted in FIG. 4 may provide an enhanced experience to the use using a computing device, and thus, may provide a technical improvement. The information that is arranged and presented on the user interface may provide the user with information that they desire without having to search other user interfaces or switching between software applications, thereby saving computing resources.

As illustrated in the example embodiment of FIG. 5, the coach display 500 includes the interval list display 536, an interval timeline 502 displaying a history of the intervals performed ideally, a coach tile 504, a set of athlete tiles 506, and a ranking region 508. According to the example embodiment, the set of athlete tiles 506 is disposed in a center of the coach display 500, with the ranking region 508 and the interval list display 536 disposed on either side of the set of athlete tiles 506. The ideal interval timeline 502 is disposed above a top side of the set of athlete tiles 506, and the coach tile 504 may be disposed in a corner of the coach display 500. Class data 510 may be presented along the top of the coach display 500 as a string of numbers associated with the class average, such as average power output, the average percent of lactic threshold of the class, and the compliance (e.g., in the form of a percentage) of the average percent of lactic threshold relative to the ideal lactic threshold percentage as identified by the interval. Additional class data 510 may be available for the coach to select for viewing on the coach display 500. In general, the coach display 500 provides the coach with an overview of the performance of each athlete exercising, as well as an overview of a performance the class as a whole.

Each of set of athlete tiles 506 is associated with one athlete and includes a video feed of that athlete, the athlete's name 514 or other moniker/screenname associated with the athlete, and performance data 432 associated with that athlete. As such, the coach, as well as other athletes with access to the coach display 500, may view, in real-time or near real-time, the progress of all of the athletes in the class. In some embodiments, due to the class size, athlete tiles 506 are disposed on other sub-displays of the coach display 500, and the user may toggle between sub-screens to view particular athlete tiles 506. The athlete tiles 506 may be color-coded for compliance to the current prescribed workout step so that the coach can easily determine how well individual athletes, and the class as a whole, is/are performing at any given time. The coach tile 504, although pertaining to the coach of the workout session in particular, is functionally equivalent to the athlete tiles 506 in terms of the video feed 512, data presented 516, and name/moniker 514. In some embodiments, however, toggling between sub-screens does not change the presence of the coach tile 504. In other words, the coach tile 504 may be statically present on the coach display 500 regardless of the particular sub-screen selected. It should be appreciated that the coaching display 500 may be configured with camera, audio, and microphone control similar to software for running Zoom, WebEx, and the like.

The ranking region 508 of the coach display 500, as illustrated in the example embodiment, may include at least one leaderboard 518, 520, 522 that provides a rank to top performers of the class. The at least one leaderboard may include a power leaderboard 518, an accuracy leaderboard 520, and a compliance leaderboard 522. Each leaderboard 518, 520, 522 is configured to present a select number (for example, 5) of athletes determined to be top performers. The ranking of each athlete on the power leaderboard 518 may be based on the amount of power each athlete has output since the start of the workout. The ranking of each athlete on the accuracy leaderboard 520 may be based on how accurate the athlete's power or energy output is relative to the power level associated with each power interval, and the compliance leaderboard 522 may be based on the level of lactic threshold compliance each athlete has achieved, as a running average, as required for each interval. Class average compliance data 524 associated with each interval, as well as the average of all executed intervals, may also be displayed in the ranking region 508. The ranking region 508 may also include at least one athlete name 514 associated with noteworthy metrics, such as compliance with personal records (e.g., to encourage improving metrics such as lactate threshold), as well as personal record lap or interval times.

The user interface depicted in FIG. 5 may provide an enhanced experience to the use using a computing device, and thus, may provide a technical improvement. The information that is arranged and presented on the user interface may provide the user with information that they desire without having to search other user interfaces or switching between software applications, thereby saving computing resources.

Figure 6:
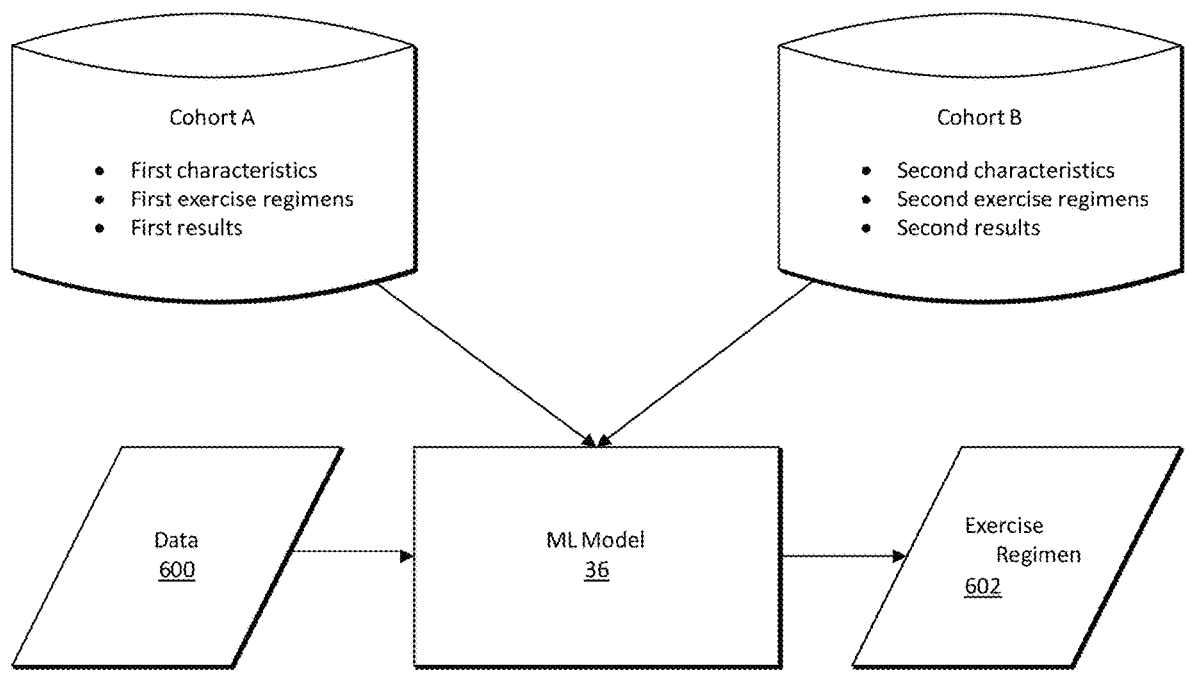
FIG. 6 generally illustrates an example block diagram of training a machine learning model to output, based on data pertaining to the athlete, an exercise regimen for the athlete according to the principles of the present disclosure.

FIG. 6 generally illustrates an example block diagram of training a machine learning model 36 to output, based on data 600 pertaining to the athlete, an exercise regimen 602 for the athlete according to the present disclosure. Data pertaining to other athletes may be received by the server 12. The other athletes may have used various exercise devices 18 to perform exercise regiments. The data may include characteristics of the other athletes, the details of the exercise regimens performed by the other athletes, and/or the results of performing the exercise regimens As depicted, the data has been assigned to different cohorts. Cohort A includes data for athletes having similar first characteristics, first exercise regimens, and first results. Cohort B includes data for patients having similar second characteristics, second exercise regimens, and second results. For example, cohort A may include first characteristics of male athletes in their twenties with a body-fat percentage of under 15%

Cohort A and cohort B may be included in a training dataset used to train the machine learning model 36. The machine learning model 36 may be trained to match a pattern between characteristics for each cohort and output the exercise regimen or a variety of possible exercise regimens for selection by a coach that provides the result. Accordingly, when the data 600 for a new patient is input into the trained machine learning model 36, the trained machine learning model 36 may match the characteristics included in the data 600 with characteristics in either cohort A or cohort B and output the appropriate exercise regimens 602. In some embodiments, the machine learning model 36 may be trained to output one or more excluded exercise regimens 602 that should not be performed by the new patient.

Figure 7:
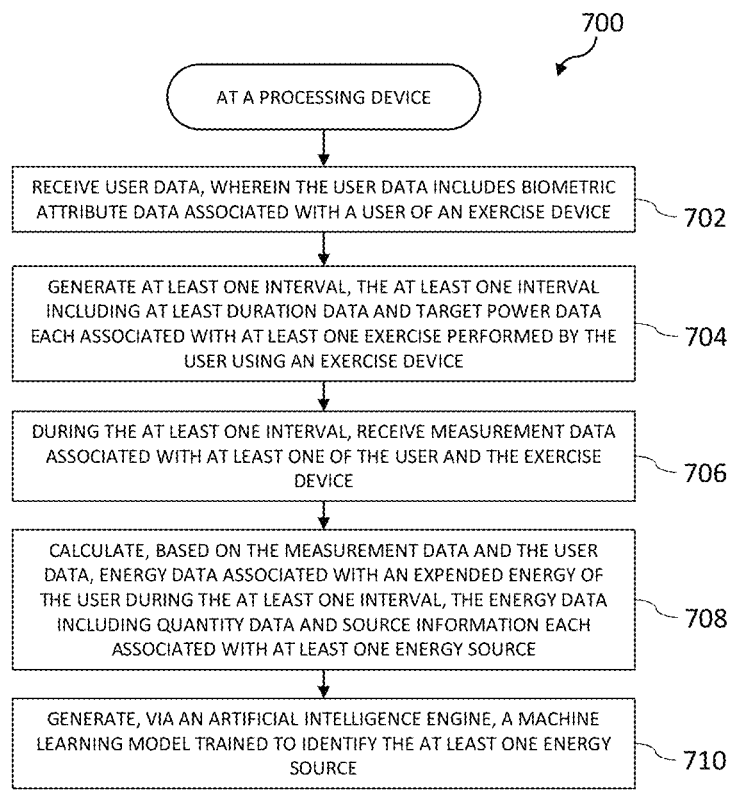
FIG. 7 is a flow diagram generally illustrating a method for optimizing at least one exercise according to the principles of the present disclosure.

FIG. 7 is a flow diagram generally illustrating a method 700 for optimizing at least one exercise for a user using an exercise device 18 according to the principles of the present disclosure. The method 700 is performed by processing logic that may include hardware (circuitry, dedicated logic, etc.), software (such as is run on a general-purpose computer system or a dedicated machine), or a combination of both. The method 700 and/or each of its individual functions, routines, subroutines, or operations may be performed by one or more processors of a computing device (e.g., any component of FIG. 1, such as server 12 executing the artificial intelligence engine 34). In some embodiments, the method 700 may be performed by a single processing thread. Alternatively, the method 700 may be performed by two or more processing threads, each thread implementing one or more individual functions, routines, subroutines, object oriented methods, or operations of the methods.

For simplicity of explanation, the methods 700, 800, 900, and 1000 are depicted and described below as a series of operations. However, operations in accordance with this disclosure can occur in various orders and/or concurrently, and/or with other operations not presented and described herein. For example, the operations depicted in the methods 700, 800, 900, and 1000 may occur in combination with any other operation of any other method disclosed herein. Furthermore, not all illustrated operations may be required to implement the methods 700, 800, 900, and 1000 in accordance with the disclosed subject matter. In addition, those skilled in the art will understand and appreciate that the methods 700, 800, 900, and 1000 could alternatively be represented as a series of interrelated states via a state diagram or events.

In some embodiments, the exercise device 18 may present to the user and coach of the energy system in use at a particular time based on the current effort based on the biometric data. This may enable presenting to the user how much fat/carbs he is burning at that moment and overall At 702, the processing device may receive user data. The user data may include biometric attribute data associated with a user of an exercise device 18. The biometric attribute data may include a body weight, a height, a sex, a body fat ratio, a sleep pattern, a resting heart rate, a heart rate variability, a blood glucose level, or a body temperature.

At 704, the processing device may generate at least one interval. The at least one interval may include at least duration data and target power data each associated with at least one exercise performed by the user using an exercise device 18.

At 706, the processing device may, during the at least one interval, receive measurement data associated with at least one of the user and the exercise device 18. The at least one interval may include a first interval and a second interval. Either the duration data associated with the first interval may be different than the duration data associated with the second interval, or the target power data associated with the first interval may be different than the target power data associated with the second interval. The measurement data may be a force applied to at least a portion of the exercise device.

At 708, the processing device may calculate, based on the measurement data and the user data, energy data associated with an expended energy of the user during the at least one interval. The energy data may include quantity data and source information each associated with at least one energy source. The at least one identified energy source may include at least one of a carbohydrate, a lipid, and a protein.

At 710, the processing device may generate, via an artificial intelligence engine 34, a machine learning model 36 trained to identify the at least one energy source. [see comment above re 710, 810, etc]

The processing device may present, on a user interface associated with the exercise, the quantity data and source information associated with at least one identified energy source. The processing device may calculate an energy source ratio, the energy source ratio being defined by a ratio of the quantity data associated with one of the at least one identified energy source to the quantity data associated with another one of the at least one identified energy source. The processing device may present the energy source ratio on the user interface while the user performs the exercise.

The processing device may generate, via the artificial intelligence engine 34 and based on the measurement data and the user data, a machine learning model 36 trained to identify lactate accumulation data associated with the lactate accumulation of the user while the user uses the exercise device 18. The processing device may present the lactate accumulation data on the user interface while the user performs the exercise. The processing device may generate, via the artificial intelligence engine 34 and based on the measurement data and the user data, a machine learning model 36 trained to identify lactate threshold data associated with a lactate threshold of the user. The processing device may to present, on the user interface, the lactate threshold data while the user performs the exercise.

Figure 8:
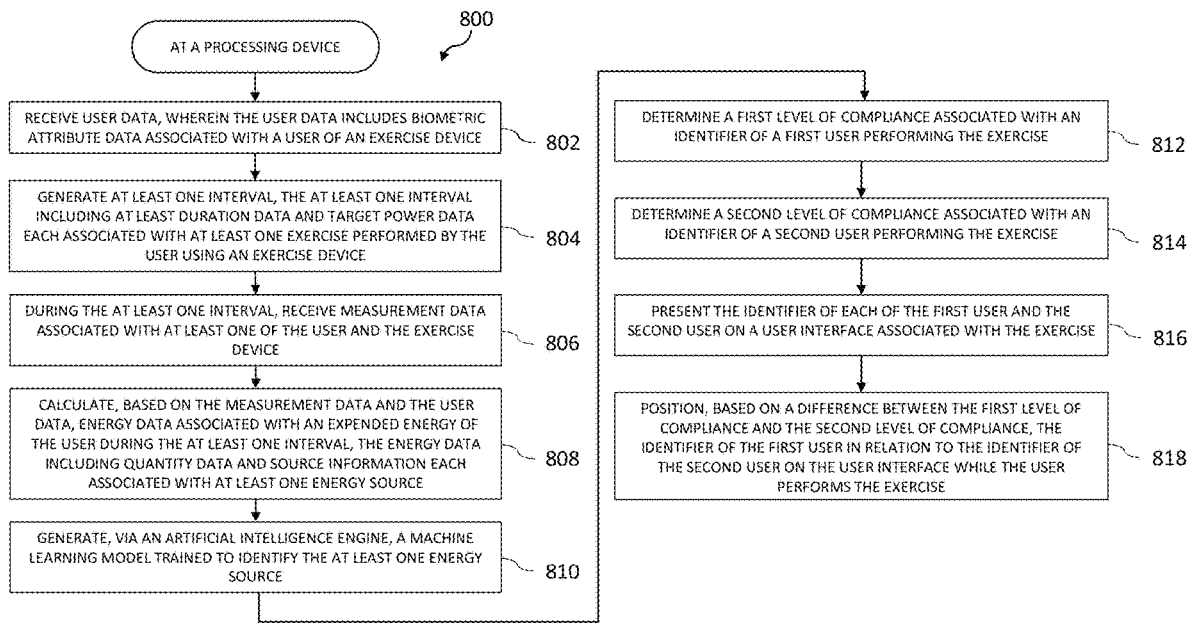
FIG. 8 is a flow diagram generally illustrating a method for optimizing at least one exercise according to the principles of the present disclosure.

FIG. 8 is a flow diagram generally illustrating an alternative method 800 for optimizing at least one exercise for a user using an exercise device 18 according to the principles of the present disclosure. Method 800 includes operations performed by processors of a computing device (e.g., any component of FIG. 1, such as server 12 executing the artificial intelligence engine 34). In some embodiments, one or more operations of the method 800 are implemented in computer instructions stored on a memory device and executed by a processing device. The method 800 may be performed in the same or a similar manner as described above in regard to method 700. The operations of the method 800 may be performed in some combination with any of the operations of any of the methods described herein.

At 802, the processing device may receive user data. The user data may include biometric attribute data associated with a user of an exercise device 18. The biometric attribute data may include a body weight, a height, a sex, a body fat ratio, a sleep pattern, a resting heart rate, a heart rate variability, a blood glucose level, or a body temperature.

At 804, the processing device may generate at least one interval. The at least one interval may include at least duration data and target power data each associated with at least one exercise performed by the user using an exercise device 18.

At 806, the processing device may, during the at least one interval, receive measurement data associated with at least one of the user and the exercise device 18. The at least one interval may include a first interval and a second interval. Either the duration data associated with the first interval may be different than the duration data associated with the second interval, or the target power data associated with the first interval may be different than the target power data associated with the second interval. The measurement data may be a force applied to at least a portion of the exercise device.

At 808, the processing device may calculate, based on the measurement data and the user data, energy data associated with an expended energy of the user during the at least one interval. The energy data may include quantity data and source information each associated with at least one energy source. The at least one identified energy source may include at least one of a carbohydrate, a lipid, and a protein.

At 810, the processing device may generate, via an artificial intelligence engine 34, a machine learning model 36 trained to identify the at least one energy source.

At 812, the processing device may determine a first level of compliance associated with an identifier of a first user performing the exercise. For example, the identifier may be the first user's name or other moniker/screenname associated with the first user. The level of compliance may be associated with a difference between an ideal position and an actual position of the user, actual power output and a target power output, actual energy usage and a target energy usage, an actual quantity of energy from a particular source (e.g. carbohydrates) and an ideal quantity of energy from that source, or any deviation between a goal and a measured or estimated value associated with a workout.

At 814, the processing device may determine a second level of compliance associated with an identifier of a second user performing the exercise. For example, the identifier may be the second user's name or other moniker/screenname associated with the second user. The level of compliance may be associated with a difference between an ideal position and an actual position of the user, actual power output and a target power output, actual energy usage and a target energy usage, an actual quantity of energy from a particular source (e.g. carbohydrates) and an ideal quantity of energy from that source, or any deviation between a goal and a measured or estimated value associated with a workout.

At 816, the processing device may present the identifier of each of the first user and the second user on a user interface associated with the exercise.

At 818, the processing device may position, based on a difference between the first level of compliance and the second level of compliance. The identifier of the first user may be in relation to the identifier of the second user on the user interface while the user performs the exercise. For example, if, initially, the first user's name is ranked in a "1" position of a leaderboard 518, 520, 522, and the second user's name is ranked in a "2" position of the leaderboard 518, 520, 522, and the level second level of compliance later exceeds the first level of compliance, the second user's name may be moved to the "1" position of a leaderboard 518, 520, 522, and the first user's name may be moved to the "2" position of the leaderboard 518, 520, 522.

Figure 9:
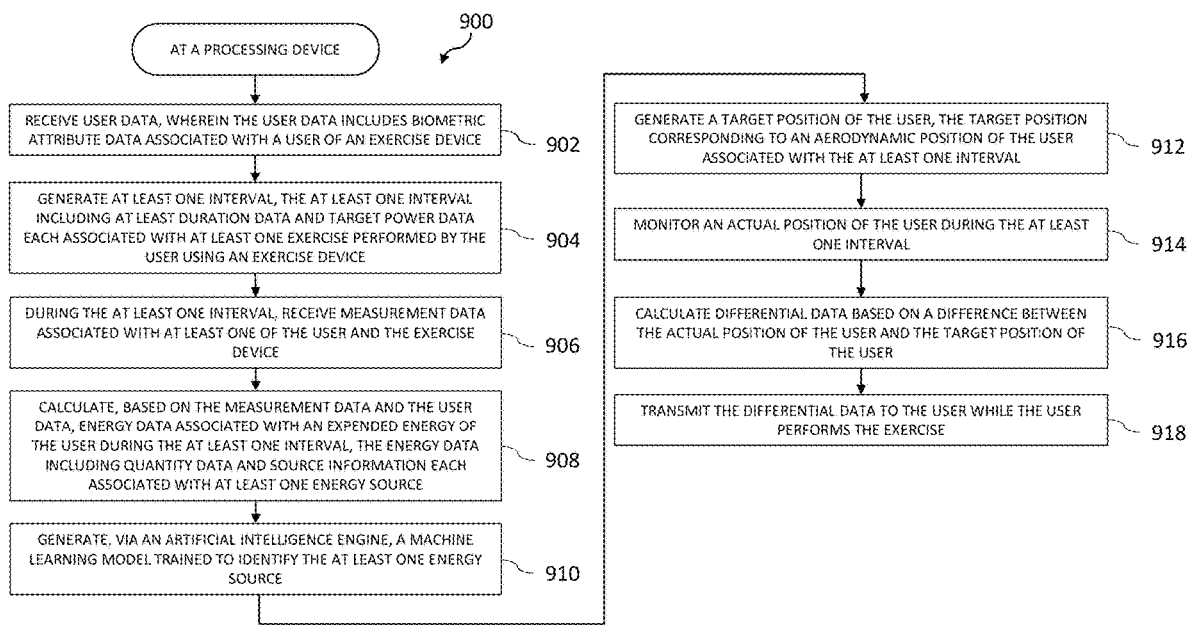
FIG. 9 is a flow diagram generally illustrating a method for optimizing at least one exercise according to the principles of the present disclosure.

FIG. 9 is a flow diagram generally illustrating an alternative method 900 for optimizing at least one exercise for a user using an exercise device 18 according to the principles of the present disclosure. Method 900 includes operations performed by processors of a computing device (e.g., any component of FIG. 1, such as server 12 executing the artificial intelligence engine 34). In some embodiments, one or more operations of the method 900 are implemented in computer instructions stored on a memory device and executed by a processing device. The method 900 may be performed in the same or a similar manner as described above in regard to method 700. The operations of the method 900 may be performed in some combination with any of the operations of any of the methods described herein.

At 902, the processing device may receive user data. The user data may include biometric attribute data associated with a user of an exercise device 18. The biometric attribute data may include a body weight, a height, a sex, a body fat ratio, a sleep pattern, a resting heart rate, a heart rate variability, a blood glucose level, or a body temperature.

At 904, the processing device may generate at least one interval. The at least one interval may include at least duration data and target power data each associated with at least one exercise performed by the user using an exercise device 18.

At 906, the processing device may, during the at least one interval, receive measurement data associated with at least one of the user and the exercise device 18. The at least one interval may include a first interval and a second interval. Either the duration data associated with the first interval may be different than the duration data associated with the second interval, or the target power data associated with the first interval may be different than the target power data associated with the second interval. The measurement data may be a force applied to at least a portion of the exercise device.

At 908, the processing device may calculate, based on the measurement data and the user data, energy data associated with an expended energy of the user during the at least one interval. The energy data may include quantity data and source information each associated with at least one energy source. The at least one identified energy source may include at least one of a carbohydrate, a lipid, and a protein.

At 910, the processing device may generate, via an artificial intelligence engine 34, a machine learning model 36 trained to identify the at least one energy source.

At 912, the processing device may generate a target position of the user, the target position corresponding to an aerodynamic position of the user associated with the at least one interval.

At 914, the processing device may monitor an actual position of the user during the at least one interval. For example, the user's physical position may be determined based on a front-facing or other view-associated camera in communication with or otherwise connected to the athlete interface 16. Video data provided by the front-facing camera, may be compared to ideal positional data stored on the server 12, the athlete interface 16, or any other component shown or described in FIG. 1.

At 916, the processing device may calculate differential data based on a difference between the actual position of the user and the target position of the user. For example, differential data may be generated based on the comparison in the example associated with step 914.

At 918, the processing device may transmit the differential data to the user while the user performs the exercise. For example, a coach may verbally or otherwise communicate the differential data in terms of specific physiological changes needed to optimize position.

Figure 10:
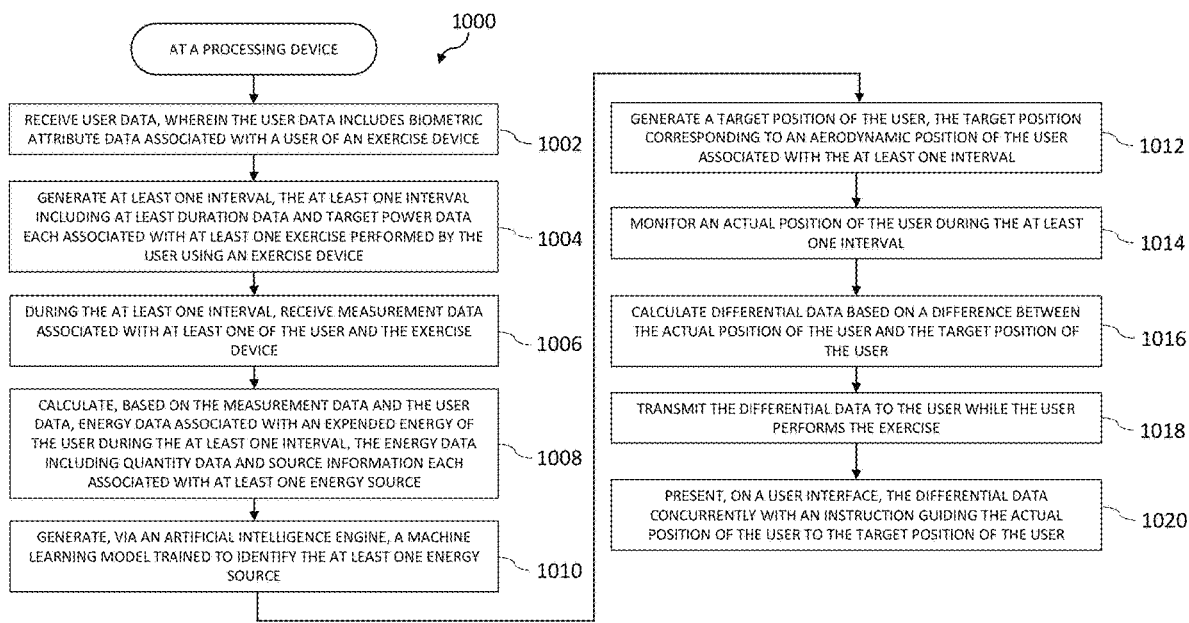
FIG. 10 is a flow diagram generally illustrating a method for optimizing at least one exercise according to the principles of the present disclosure.

FIG. 10 is a flow diagram generally illustrating an alternative method 1000 for optimizing at least one exercise for a user using an exercise device 18 according to the principles of the present disclosure. Method 1000 includes operations performed by processors of a computing device (e.g., any component of FIG. 1, such as server 12 executing the artificial intelligence engine 34). In some embodiments, one or more operations of the method 1000 are implemented in computer instructions stored on a memory device and executed by a processing device. The method 1000 may be performed in the same or a similar manner as described above in regard to method 700. The operations of the method 1000 may be performed in some combination with any of the operations of any of the methods described herein.

At 1002, the processing device may receive user data. The user data may include biometric attribute data associated with a user of an exercise device 18. The biometric attribute data may include a body weight, a height, a sex, a body fat ratio, a sleep pattern, a resting heart rate, a heart rate variability, a blood glucose level, or a body temperature.

At 1004, the processing device may generate at least one interval. The at least one interval may include at least duration data and target power data each associated with at least one exercise performed by the user using an exercise device 18.

At 1006, the processing device may, during the at least one interval, receive measurement data associated with at least one of the user and the exercise device 18. The at least one interval may include a first interval and a second interval. Either the duration data associated with the first interval may be different than the duration data associated with the second interval, or the target power data associated with the first interval may be different than the target power data associated with the second interval. The measurement data may be a force applied to at least a portion of the exercise device.

At 1008, the processing device may calculate, based on the measurement data and the user data, energy data associated with an expended energy of the user during the at least one interval. The energy data may include quantity data and source information each associated with at least one energy source. The at least one identified energy source may include at least one of a carbohydrate, a lipid, and a protein.

At 1010, the processing device may generate, via an artificial intelligence engine 34, a machine learning model 36 trained to identify the at least one energy source.

At 1012, the processing device may generate a target position of the user, the target position corresponding to an aerodynamic position of the user associated with the at least one interval.

At 1012, the processing device may monitor an actual position of the user during the at least one interval. For example, the user's physical position may be determined based on a front-facing or other view-associated camera in communication with or otherwise connected to the athlete interface 16. Video data provided by the front-facing camera, may be compared to ideal positional data stored on the server 12, the athlete interface 16, or any other component shown or described in FIG. 1.

At 1016, the processing device may calculate differential data based on a difference between the actual position of the user and the target position of the user. For example, differential data may be generated based on the comparison in the example associated with step 914.

At 1018, the processing device may transmit the differential data to the user while the user performs the exercise.

At 1020, the processing device may present, on a user interface, the differential data concurrently with an instruction guiding the actual position of the user to the target position of the user. For example, differential data may be presented to the user in the form of a compliance score, or a video of the athlete overlaid with an outline of the ideal position may be presented.

Figure 11:
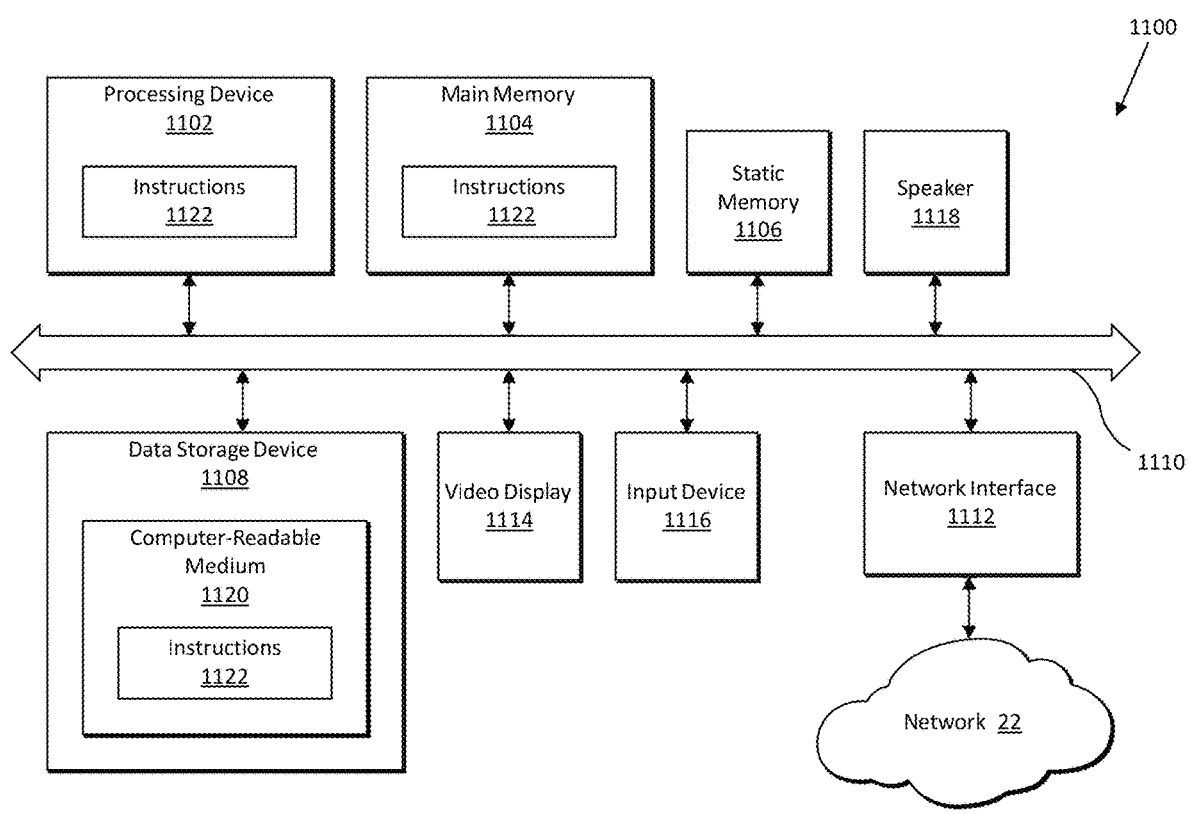
FIG. 11 generally illustrates a computer system according to the principles of the present disclosure.

FIG. 11 shows an example computer system 1100, which can perform any one or more of the methods described herein, in accordance with one or more aspects of the present disclosure. In one example, computer system 1100 may include a computing device and correspond to the server 12 (including the AI engine 34), athlete interface 16, exercise device 18, or any suitable component of FIG. 1. The computer system 1100 may be capable of executing instructions implementing the one or more machine learning models 36 of the artificial intelligence engine 34 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1100 includes a processing device 1102, a main memory 1104 (e.g., read-only memory (ROM), flash memory, solid state drives (SSDs), dynamic random access memory (DRAM) such as synchronous DRAM (SDRAM)), a static memory 1106 (e.g., flash memory, solid state drives (SSDs), static random access memory (SRAM)), and a data storage device 1108, which communicate with each other via a bus 1110.

Processing device 1102 represents one or more general-purpose processing devices such as a microprocessor, central processing unit, or the like. More particularly, the processing device 1102 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1102 may also be one or more special-purpose processing devices such as an application specific integrated circuit (ASIC), a system on a chip, a field programmable gate array (FPGA), a digital signal processor (DSP), network processor, or the like. The processing device 1102 is configured to execute instructions for performing any of the operations and steps discussed herein.

The computer system 1100 may further include a network interface device 1112. The computer system 1100 also may include a video display 1114 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1116 (e.g., a keyboard and/or a mouse or a gaming-like control), and one or more speakers 1118 (e.g., a speaker). In one illustrative example, the video display 1114 and the input device(s) 1116 may be combined into a single component or device (e.g., an LCD touch screen).

The data storage device 1116 may include a computer-readable medium 1120 on which the instructions 1122 embodying any one or more of the methods, operations, or functions described herein is stored. The instructions 1122 may also reside, completely or at least partially, within the main memory 1104 and/or within the processing device 1102 during execution thereof by the computer system 1100. As such, the main memory 1104 and the processing device 1102 also constitute computer-readable media. The instructions 1122 may further be transmitted or received over the network 22 via the network interface device 1112.

While the computer-readable storage medium 1100 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A method for optimizing at least one exercise performed by a user using an exercise device, the method comprising: receiving user data, wherein the user data includes biometric attribute data associated with the user of the exercise device; generating at least one interval, the at least one interval including at least duration data and target power data each associated with the exercise; during the at least one interval, receiving measurement data associated with at least one of the user and the exercise device; calculating, based on the measurement data and the user data, energy data associated with an expended energy of the user during the at least one interval, the energy data including quantity data and source information each associated with at least one energy source; and generating, via an artificial intelligence engine, a machine learning model trained to identify the at least one energy source.

Clause 2. The method of clause 1, further comprising presenting, on a user interface associated with the exercise, the quantity data and source information associated with at least one identified energy source.

Clause 3. The method of clause 2, wherein the at least one identified energy source includes at least one of a carbohydrate, a lipid, and a protein.

Clause 4. The method of clause 2, further comprising calculating an energy source ratio, the energy source ratio being defined by a ratio of the quantity data associated with one of the at least one identified energy source to the quantity data associated with another one of the at least one identified energy source; and presenting the energy source ratio on the user interface while the user performs the exercise.

Clause 5. The method of clause 2, further comprising generating, via an artificial intelligence engine and based on the measurement data and the user data, a machine learning model trained to identify lactate accumulation data associated with the lactate accumulation of the user while the user uses the exercise device; and presenting the lactate accumulation data on the user interface while the user performs the exercise.

Clause 6. The method of clause 2, further comprising generating, via an artificial intelligence engine and based on the measurement data and the user data, a machine learning model trained to identify lactate threshold data associated with a lactate threshold of the user; and presenting, on the user interface, the lactate threshold data while the user performs the exercise.

Clause 7. The method of clause 1, wherein the at least one interval includes a first interval and a second interval, and wherein either the duration data associated with the first interval is different than the duration data associated with the second interval or the target power data associated with the first interval is different than the target power data associated with the second interval.

Clause 8. The method of clause 1, further comprising: determining a first level of compliance associated with an identifier of a first user performing the exercise; determining a second level of compliance associated with an identifier of a second user performing the exercise; presenting the identifier of each of the first user and the second user on a user interface associated with the exercise; and positioning, based on a difference between the first level of compliance and the second level of compliance, the identifier of the first user in relation to the identifier of the second user on the user interface while the user performs the exercise.

Clause 9. The method of clause 1, further comprising: generating a target position of the user, the target position corresponding to an aerodynamic position of the user associated with the at least one interval; monitoring an actual position of the user during the at least one interval; calculating differential data based on a difference between the actual position of the user and the target position of the user; and transmitting the differential data to the user while the user performs the exercise.

Clause 10. The method of clause 9, further comprising presenting, on a user interface, the differential data concurrently with an instruction guiding the actual position of the user to the target position of the user.

Clause 11. A tangible, non-transitory computer-readable medium storing instructions that, when executed, cause a processing device to: receive user data, wherein the user data includes biometric attribute data associated with a user of an exercise device; generate at least one interval, the at least one interval including at least duration data and target power data each associated with at least one exercise performed by the user using an exercise device; during the at least one interval, receive measurement data associated with at least one of the user and the exercise device; calculate, based on the measurement data and the user data, energy data associated with an expended energy of the user during the at least one interval, the energy data including quantity data and source information each associated with at least one energy source; and generate, via an artificial intelligence engine, a machine learning model trained to identify the at least one energy source.

Clause 12. The method of clause 11, wherein the processing device is further to present, on a user interface associated with the exercise, the quantity data and source information associated with at least one identified energy source.

Clause 13. The method of clause 11, wherein the processing device is further to: determine a first level of compliance associated with an identifier of a first user performing the exercise; determine a second level of compliance associated with an identifier of a second user performing the exercise; present the identifier of each of the first user and the second user on a user interface associated with the exercise; and position, based on a difference between the first level of compliance and the second level of compliance, the identifier of the first user in relation to the identifier of the second user on the user interface while the user performs the exercise.

Clause 14. The method of clause 11, wherein the processing device is further to: generate a target position of the user, the target position corresponding to an aerodynamic position of the user associated with the at least one interval; monitor an actual position of the user during the at least one interval; calculate differential data based on a difference between the actual position of the user and the target position of the user; and transmit the differential data to the user while the user performs the exercise.

Clause 15. The method of clause 14, wherein the processing device is further to present, on a user interface, the differential data concurrently with an instruction guiding the actual position of the user to the target position of the user.

Clause 16. A system for optimizing at least one exercise performed by a user using an exercise device, the system comprising: a memory device storing instructions; a processing device communicatively coupled to the memory device, the processing device executes the instructions to: receive user data, wherein the user data includes biometric attribute data associated with a user of an exercise device; generate at least one interval, the at least one interval including at least duration data and target power data each associated with at least one exercise performed by the user using an exercise device; during the at least one interval, receive measurement data associated with at least one of the user and the exercise device; calculate, based on the measurement data and the user data, energy data associated with an expended energy of the user during the at least one interval, the energy data including quantity data and source information each associated with at least one energy source; and generate, via an artificial intelligence engine, a machine learning model trained to identify the at least one energy source.

Clause 17. The method of clause 16, wherein the processing device is further to present, on a user interface associated with the exercise, the quantity data and source information associated with at least one identified energy source.

Clause 18. The method of clause 16, wherein the processing device is further to: determine a first level of compliance associated with an identifier of a first user performing the exercise; determine a second level of compliance associated with an identifier of a second user performing the exercise; present the identifier of each of the first user and the second user on a user interface associated with the exercise; and position, based on a difference between the first level of compliance and the second level of compliance, the identifier of the first user in relation to the identifier of the second user on the user interface while the user performs the exercise.

Clause 19. The method of clause 16, wherein the processing device is further to: generate a target position of the user, the target position corresponding to an aerodynamic position of the user associated with the at least one interval; monitor an actual position of the user during the at least one interval; calculate differential data based on a difference between the actual position of the user and the target position of the user; and transmit the differential data to the user while the user performs the exercise.

Clause 20. The method of clause 19, wherein the processing device is further to present, on a user interface, the differential data concurrently with an instruction guiding the actual position of the user to the target position of the user.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A method for optimizing at least one exercise performed by a user using an exercise device, the method comprising:
   receiving user data, wherein the user data includes biometric attribute data associated with the user of the exercise device;
   generating at least one interval, the at least one interval including at least duration data and target power data each associated with the exercise;
   during the at least one interval, receiving measurement data associated with at least one of the user and the exercise device;
   calculating, based on the measurement data and the user data, energy data associated with an expended energy of the user during the at least one interval, the energy data including quantity data and source information each associated with at least one energy source; and
   generating, via an artificial intelligence engine, a machine learning model trained to identify the at least one energy source.

2. The method of claim 1, further comprising presenting, on a user interface associated with the exercise, the quantity data and source information associated with at least one identified energy source.

3. The method of claim 2, wherein the at least one identified energy source includes at least one of a carbohydrate and a lipid.

4. The method of claim 2, further comprising calculating an energy source ratio, the energy source ratio being defined by a ratio of the quantity data associated with one of the at least one identified energy source to the quantity data associated with another one of the at least one identified energy source; and
   presenting the energy source ratio on the user interface while the user performs the exercise.

5. The method of claim 2, further comprising generating, via an artificial intelligence engine and based on the measurement data and the user data, a machine learning model trained to identify lactate accumulation data associated with the lactate accumulation of the user while the user uses the exercise device; and
   presenting the lactate accumulation data on the user interface while the user performs the exercise.

6. The method of claim 2, further comprising generating, via an artificial intelligence engine and based on the measurement data and the user data, a machine learning model trained to identify lactate threshold data associated with a lactate threshold of the user; and
   presenting, on the user interface, the lactate threshold data while the user performs the exercise.

7. The method of claim 1, wherein the at least one interval includes a first interval and a second interval, and wherein either the duration data associated with the first interval is different than the duration data associated with the second interval or the target power data associated with the first interval is different than the target power data associated with the second interval.

8. The method of claim 1, further comprising:
   determining a first level of compliance associated with an identifier of a first user performing the exercise;
   determining a second level of compliance associated with an identifier of a second user performing the exercise;
   presenting the identifier of each of the first user and the second user on a user interface associated with the exercise; and
   positioning, based on a difference between the first level of compliance and the second level of compliance, the identifier of the first user in relation to the identifier of the second user on the user interface while the user performs the exercise.

9. The method of claim 8 wherein the at least one interval is based on at least one of the first level of compliance and the second level of compliance.

10. The method of claim 1, further comprising:
    generating a target position of the user, the target position corresponding to an aerodynamic position of the user associated with the at least one interval;
    monitoring an actual position of the user during the at least one interval;
    calculating differential data based on a difference between the actual position of the user and the target position of the user; and
    transmitting the differential data to the user while the user performs the exercise.

11. The method of claim 10, further comprising presenting, on a user interface, the differential data concurrently with an instruction guiding the actual position of the user to the target position of the user.

12. A tangible, non-transitory computer-readable medium storing instructions that, when executed, cause a processing device to:
    receive user data, wherein the user data includes biometric attribute data associated with a user of an exercise device;
    generate at least one interval, the at least one interval including at least duration data and target power data each associated with at least one exercise performed by the user using an exercise device;
    during the at least one interval, receive measurement data associated with at least one of the user and the exercise device;
    calculate, based on the measurement data and the user data, energy data associated with an expended energy of the user during the at least one interval, the energy data including quantity data and source information each associated with at least one energy source; and
    generate, via an artificial intelligence engine, a machine learning model trained to identify the at least one energy source.

13. The computer-readable medium of claim 12, wherein the processing device is further to present, on a user interface associated with the exercise, the quantity data and source information associated with at least one identified energy source.

14. The computer-readable medium of claim 12, wherein the processing device is further to:
    determine a first level of compliance associated with an identifier of a first user performing the exercise;
    determine a second level of compliance associated with an identifier of a second user performing the exercise;
    present the identifier of each of the first user and the second user on a user interface associated with the exercise; and
    position, based on a difference between the first level of compliance and the second level of compliance, the identifier of the first user in relation to the identifier of the second user on the user interface while the user performs the exercise.

15. The computer-readable medium of claim 12, wherein the processing device is further to:
generate a target position of the user, the target position corresponding to an aerodynamic position of the user associated with the at least one interval;
monitor an actual position of the user during the at least one interval;
calculate differential data based on a difference between the actual position of the user and the target position of the user; and
transmit the differential data to the user while the user performs the exercise.

16. The computer-readable medium of claim 15, wherein the processing device is further to present, on a user interface, the differential data concurrently with an instruction guiding the actual position of the user to the target position of the user.

17. A system for optimizing at least one exercise performed by a user using an exercise device, the system comprising:
a memory device storing instructions;
a processing device communicatively coupled to the memory device, the processing device executes the instructions to:
receive user data, wherein the user data includes biometric attribute data associated with a user of an exercise device;
generate at least one interval, the at least one interval including at least duration data and target power data each associated with at least one exercise performed by the user using an exercise device;
during the at least one interval, receive measurement data associated with at least one of the user and the exercise device;
calculate, based on the measurement data and the user data, energy data associated with an expended energy of the user during the at least one interval, the energy data including quantity data and source information each associated with at least one energy source; and
generate, via an artificial intelligence engine, a machine learning model trained to identify the at least one energy source.

18. The system of claim 17, wherein the processing device is further to present, on a user interface associated with the exercise, the quantity data and source information associated with at least one identified energy source.

19. The system of claim 17, wherein the processing device is further to:
determine a first level of compliance associated with an identifier of a first user performing the exercise;
determine a second level of compliance associated with an identifier of a second user performing the exercise;
present the identifier of each of the first user and the second user on a user interface associated with the exercise; and
position, based on a difference between the first level of compliance and the second level of compliance, the identifier of the first user in relation to the identifier of the second user on the user interface while the user performs the exercise.

20. The system of claim 17, wherein the processing device is further to:
generate a target position of the user, the target position corresponding to an aerodynamic position of the user associated with the at least one interval;
monitor an actual position of the user during the at least one interval;
calculate differential data based on a difference between the actual position of the user and the target position of the user; and
transmit the differential data to the user while the user performs the exercise.

\* \* \* \* \*